United States Patent [19]
Nardi et al.
[11] 3,933,793
[45] Jan. 20, 1976

[54] THERAPEUTICALLY ACTIVE 2-AMINOALKYLTHIO-3H-1.5-BENZODIAZEPINES AND PROCESS FOR PREPARING THEM

[75] Inventors: Dante Nardi; Elena Massarani, both of Milan; Ludwig Degen, Rome, all of Italy

[73] Assignee: Recordati S.A. Chemical and Pharmaceutical Company, Chiasso, Switzerland

[22] Filed: Oct. 10, 1972

[21] Appl. No.: 296,045

[30] Foreign Application Priority Data

| | | |
|---|---|---|
| Oct. 19, 1971 | Italy | 30018/71 |
| May 18, 1972 | Italy | 24509/72 |

[52] U.S. Cl. 260/239 BD; 260/247.1 M; 260/268 BC; 260/298.59; 260/326.81; 424/244; 424/248; 424/250; 424/267; 424/274

[51] Int. Cl.[2] C07D 243/12

[58] Field of Search 260/239 BD, 268 BC, 260/247.1 M, 293.69, 326.81, 326.59

[56] References Cited

UNITED STATES PATENTS

| | | | |
|---|---|---|---|
| 3,595,858 | 7/1971 | McManus | 260/239.3 B |

FOREIGN PATENTS OR APPLICATIONS

| | | | |
|---|---|---|---|
| 287,728 | 2/1971 | Austria | 260/239 BD |
| 2,053,679 | 5/1972 | Germany | 260/239.3 B |
| 643,913 | 2/1964 | Belgium | 260/239.3 D |

OTHER PUBLICATIONS

Elslager et al., "J. Het. Chem.," Vol. 5, pp. 609–613 (1968).
Archer et al., "J. Org. Chem.," Vol. 29, pp. 239–233 (1964).

*Primary Examiner*—John D. Randolph
*Assistant Examiner*—Robert T. Bond
*Attorney, Agent, or Firm*—Stevens, Davis, Miller & Mosher

[57] ABSTRACT

Novel derivatives of 3H-1,5-benzodiazepine and of their salts of addition with acids, including their quaternary ammonium salts, having the general formula:

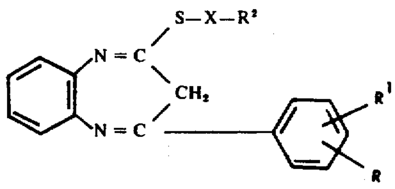

(I)

are provided. Such compounds are effective therapeutically against a large spectrum of gram positive bacteria and APR8 influenza virus. The invention also provides a novel method of preparing compounds having the formula:

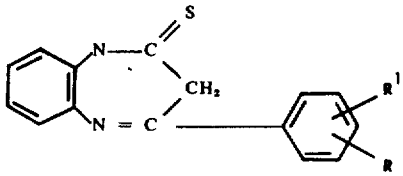

(III)

wherein R and R' are the same as above, by reacting orthophenylenediamine with a benzoyldithioacetic acid having the formula:

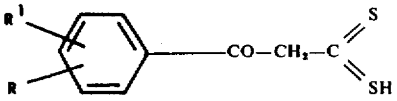

(II)

wherein R and R' are as defined above.

15 Claims, No Drawings

THERAPEUTICALLY ACTIVE 2-AMINOALKYLTHIO-3H-1.5-BENZODIAZEPINES AND PROCESS FOR PREPARING THEM

This invention relates generally to therapeutically active derivatives of 3H-1,5-benzodiazepine and more particularly to compounds of the following formula and to the acid salts and quaternary ammonium salts of such compounds:

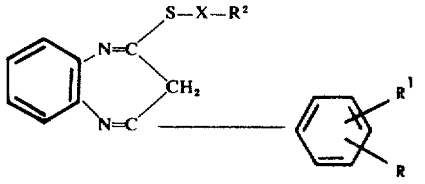

(I)

wherein:

- R represents hydrogen, halogen, methoxy, phenylthio or alkylthio group having a straight or branched chain, which may contain 1 to 12 carbon atoms;
- $R^1$ represents hydrogen, halogen, methyl, phenyl, phenoxy or alkylthio group having a straight or branched chain, which may contain 1 to 12 carbon atoms, cyclohexylthio, benzylthio or phenylthio;
- $R^2$ represents di-lower alkyl-amino group, or a substituted or unsubstituted penta- or hexa-atomic saturated cyclic amino group which, besides the nitrogen atom, by which it is bound to X, may also contain another hetero-atom;
- X represents a straight or branched alkylene chain containing 2 or 3 carbon atoms.

It is therefore an object of this invention to provide compounds of Formula I. Another object of the invention is to provide a novel method of making compounds of formula III' and of formula III hereinafter set forth.

The products of formula I have a considerable antibacterial activity against a large spectrum of gram positive bacterial, and an anti-virus activity against the APR8 influenza virus and are useful for therapeutic purposes. Particularly preferred compounds are 2,beta,N-diethylaminoethylthio-4,p-phenylthiophenyl-3H-1,5-benzodiazepine iodomethylate and 2,beta,N-diethylamineoethylthio-4,p-phenylthiophenyl-3H-1,5-benzodiazepine methyl nitrate.

According to the invention, the compounds having the formula I are prepared by successive steps which are shown in the following diagram:

The starting products for this synthesis are the benzoyldithioacetic acids having the formula

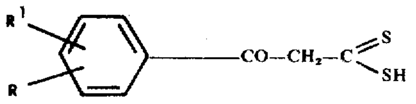

(II)

which may also exist in the tautomer form of 1-phenyl-3,3-dimercapto-2-propene-1-ones having the formula

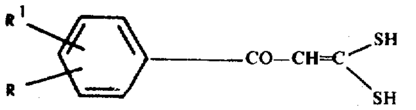

(II')

wherein R and $R^1$ are as defined above. Some of these products are already known (C. Kelber - Ber. 43, 2 (1910); G. Kelber et al Ber. 45, 137 (1912); A. Thuillier et al - Bull. Soc. Chim. Fr. 1398 (1959)).

The compounds having the formulas II and II' can be prepared by reacting the corresponding acetophenone with carbon disulfide in the presence of sodium ter. amylate.

According to the invention the compound having the formula III is obtained by heating benzoyldithioacetic acid having the formula II and o-phenylenediamine in a polar or nonpolar solvent, for example, dioxane, ethyl alcohol, benzene, toluene, xylene or even water with elimination of water and hydrogen sulfide:

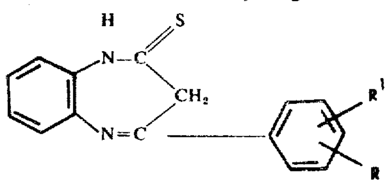

(III)

These products may also exist in the tautomer form III', for example, in the presence of NaH and in such case they may supply alkylthioderivatives:

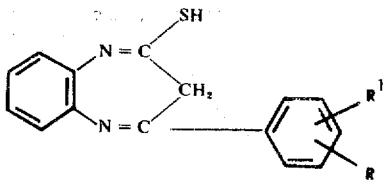

(III')

The foregoing process for preparing the compounds having the formula III is new and provided by the invention. It is known indeed that the benzodiazepinthiones are obtained by treating the corresponding benzodiazepinones with phosphorus pentasulfide.

For the introduction of the dialkylaminoalkyl group $-X-R^2$, the compounds having the formula III, are mixed with an equimolecular quantity of sodium hydride and then are treated with the corresponding dialkylaminoalkylhalide having the formula Hal-X-$R^2$, wherein X and $R^2$ are as defined above with respect to formula I and Hal represents a halogen such as chlorine, bromine in a solvent such as ethyl ether, benzene, toluene, etc., and the mixture is heated between 40°C and 130°C for a period ranging from 5 to 20 hours. After elimination of sodium halide by filtration, the solvent and the possible excess of aminoalkyl halide are removed by distillation under reduced pressure, and the products having the formula I are obtained as a free base. In most cases they are obtained as an oily residue which can be purified by crystallization (generally petroleum ether or ligroine).

Conventional methods are used to prepare the salts of addition with the acids and to prepare the quanternary ammonium salts; in particular, the latter compounds can be obtained by treating the compounds of formula I with alkyl or aralkyl halide in acetone, isopropanol or ethanol at room temperature for a period of time ranging from 15 to 96 hours until complete precipitation.

The quaternary ammonium salts may also be obtained starting from the ammonium halides obtained as said hereinabove.

One method consists in effecting a double exchange between the methyl ammonium iodide and a soluble silver salt, for example, silver nitrate, so as to obtain in this way the corresponding methyl nitrate.

Another method consists in passing a methylammonium halide solution through a column of anionic exchanger resin ($OH^-$), to free the quaternary ammonium hydroxide, and in neutralizing the latter with the theoretical quantity of acid.

The preparation of compounds having formula I may be represented by the following:

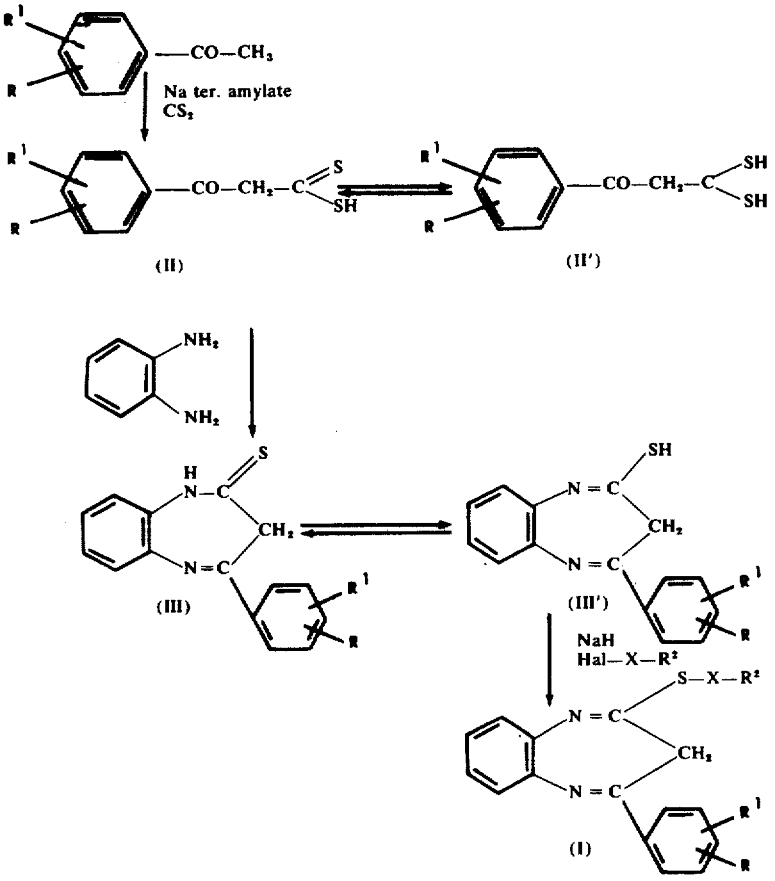
The preparation of the quaternary ammonium salts may be represented as follows:
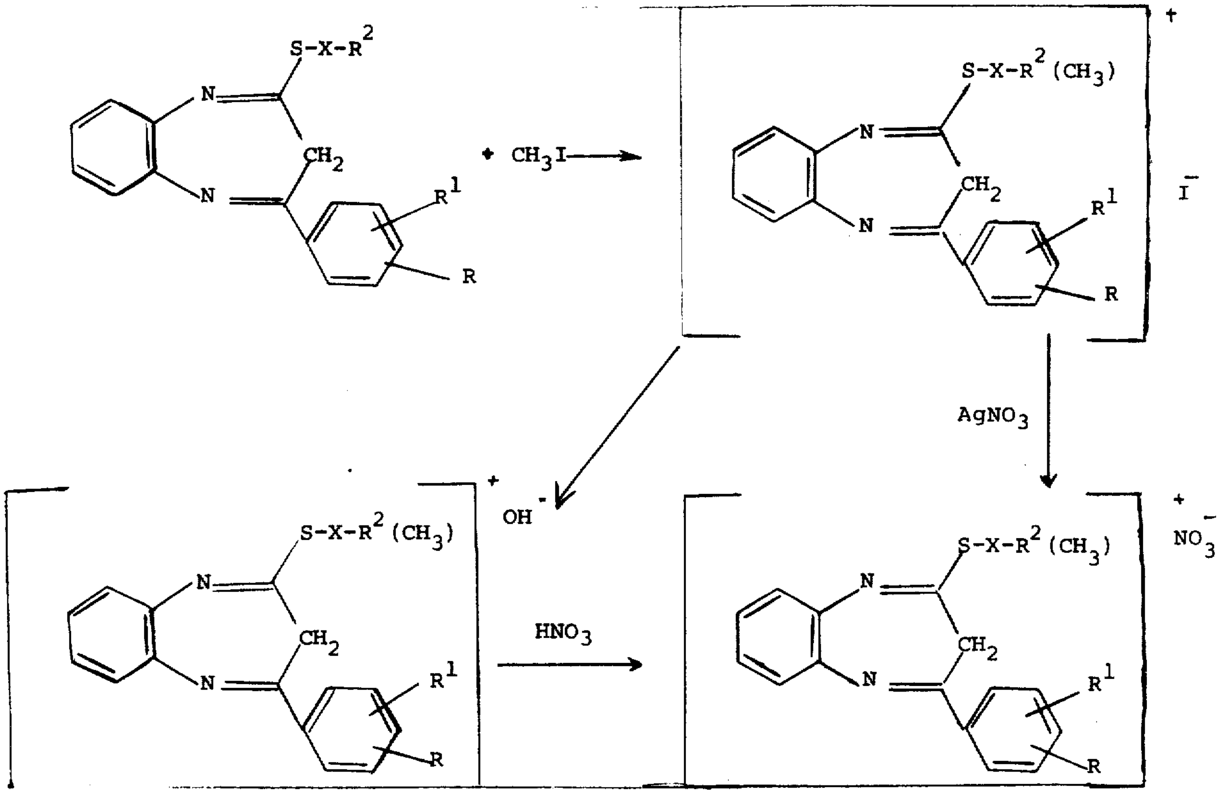

The preparation of the intermediate compounds having the formula II or II' and III or III' is illustrated by the following examples.

EXAMPLE 1

4-phenoxy-benzoyldithioacetic acid (Formula II wherein R = H and $R^1 = C_6H_5O$-)

A solution of 5.30 g of 4-acetyldiphenylether and of 1.90 g of carbon disulfide in 6 ml of benzene is added dropwise in 2.5 hours at 15°C to 50 ml of a molar benzene solution of sodium ter-amylate. The reaction mixture is then kept at 15°C for 30 min. and poured into icy water. The mixture is separated and the benzene layer is removed. The aqueous solution is washed twice with ethyl ether which is then removed. The solution is cooled, and acidified with cold diluted $H_2SO_4$. The precipitate is filtered, washed with water, and dried in a desiccator over NaOH - $P_2O_5$. Yield, 6.15 g; m.p. 78°C.

| Analysis for $C_{15}H_{12}O_2S_2$ | C | H | S |
|---|---|---|---|
| calc. % | 62.50 | 4.20 | 21.73 |
| found. % | 62.15 | 4.11 | 22.20 |

EXAMPLE 2

4-phenylthio-benzoyldithioacetic acid (Formula II wherein R = H and $R^1 = C_6H_5S$-)

A solution of 5.7 g of 4-acetyl-diphenylsulfide in 6 ml of benzene and 1.90 g of carbon disulfide is added dropwise in 2.5 hours to 50 ml of a molar benzene solution of sodium ter. amylate cooled to 15°C and the reaction is further carried out as in Example 1. Yield 7.15 g, m.p. 90°C.

| Analysis for $C_{15}H_{12}OS_3$ | C | H | S |
|---|---|---|---|
| calc. % | 59.21 | 3.98 | 31.50 |
| found. % | 58.89 | 4.22 | 31.52 |

EXAMPLE 3

4-phenyl-1.3-dihydro-2H-1.5-benzodiazepine-2-thione (Formula III wherein R and $R^1$ = H)

A mixture of 1.08 g of o-phenylendiamine, 10 ml of xylene and 1.96 g of benzoyldithioacetic acid (Thuillier et al - Bull. Soc. Chim. Fr. 1938 (1959) is refluxed for 1 hour under a stream of nitrogen. The reaction may also be carried out in water, alcohol or dioxane. After cooling, the precipitate is filtered, washed with ethyl ether, and crystallized from ethyl acetate. Yield 2 g, m.p. 228°–230°C.

| Analysis for $C_{15}H_{12}N_2S$ | C | H | N | S |
|---|---|---|---|---|
| calc. % | 71.41 | 4.80 | 11.11 | 12.69 |
| found. % | 71.44 | 5.24 | 11.14 | 13.00 |

EXAMPLE 4

4,p-chlorophynyl-1,3-dihydro-2H-1,5-benzodiazepine-2-thione (Formula III wherein R = H and $R^1$ = p-Cl)

A mixture of 1.08 g of o-phenylendiamine, 40 ml toluene and 2.14 g of 4-chorophenyl-benzoyldithioacetic acid (Thuillier et al. - Bull. Soc. Chim. Fr. 1398 (1959) ) is refluxed for 1 hour under a stream of nitrogen. After cooling, the precipitate is filtered, washed with ethyl ether, and crystallized from ethyl acetate. Yield 2.1 g, m. p. 243°–245°C.

| Analysis for $C_{15}H_{11}ClN_2S_2$ | C | H | N | S |
|---|---|---|---|---|
| calc. % | 62.84 | 3.86 | 9.77 | 11.16 |
| found. % | 62.92 | 4.16 | 9.72 | 11.28 |

EXAMPLE 5

4,p-diphenylyl-1,3-dihydro-2H-1,5-benzodiazepine-2-thione (Formula III wherein R = H and $R^1$ = p-$C_6H_5$)

A mixture of 1.08 g of o-phenylendiamine, 40 ml of toluene and 2.72 g of 4-phenyl-benzoyldithioacetic acid (Thuillier et al. - Bull. Soc. Chim. Fr. 1398 (1959) ) is refluxed for 1 hour under a stream of nitrogen. After cooling, the precipitate is filtered, washed with ethyl ether, and crystallized from ethyl acetate. Yield 2.4 g, m. p. 229°–230°C.

| Analysis for $C_{21}H_{16}N_2S$ | C | H | N | S |
|---|---|---|---|---|
| calc. % | 76.81 | 4.91 | 8.53 | 9.75 |
| found. % | 76.65 | 4.86 | 8.78 | 9.86 |

EXAMPLE 6

4,p-phenoxyphenyl-1,3-dihydro-2H-1,5-benzodiazepine-2-thione (Formula III wherein R = H and $R^1 = C_6H_5O$)

A mixture of 1.44 g of 4-phenoxy-benzoyldithioacetic acid, 0.54 g of o-phenylediamine and 20 ml of xylene is refluxed for 1.5 hours under a stream of nitrogen. Then the mixture is cooled and the resulting crystalline precipitate is filtered and re-crystallized from ethyl acetate. Yield 0.86 g, m. p. 225°C.

| Analysis for $C_{21}H_{16}N_2OS$ | C | H | N | S |
|---|---|---|---|---|
| calc. % | 73.24 | 4.68 | 8.14 | 9.29 |
| found. % | 73.27 | 4.74 | 8.02 | 9.45 |

EXAMPLE 7

4,p-phenylthiophenyl-1,3-dihydro-2H-1,5-benzodiazepine-2-thione (Formula III wherein R = H and $R^1 = C_6H_5S$)

A mixture of 1.08 g of o-phenylendiamine, 20 ml of toluene and 3.04 g of 4-phenylthio-benzoyldithioacetic acid is refluxed for 1 hour. After cooling, the mixture is filtered, the precipitate is washed with ethyl ether, and crystallized from ethyl acetate. Yield 1.8 g, m. p. 229°–230°C.

| Analysis for $C_{21}H_{16}N_2S_2$ | C | H | N | S |
|---|---|---|---|---|
| calc. % | 69.99 | 4.48 | 7.77 | 17.76 |
| found. % | 69.85 | 4.68 | 7.53 | 17.51 |

The preparation of the compounds having the formula I by the process according to the invention is illustrated by the following examples.

EXAMPLE 8

2,gamma,N(N'-methyl)piperazinopropylthio-4-phenyl-3H-1,5-benzodiazephine.2HCl (Formula I wherein R and $R^1$ = H;

$R^2$ = 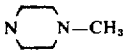

and X = $-CH_2-CH_2-CH_2-$)

A mixture of 10.08 g of 4-phenyl-1,3-dihydro-2H-1,5-benzodiazepine-2-thione, 2 g of 50 percent sodium hydride in oil and 800 ml of benzene is refluxed for 30 minutes. A solution of 10.4 g of gamma, N'-methyl-N-piperazinopropyl chloride in 20 ml of benzene is then added dropwise in 5 minutes. The mixture is refluxed for 10 hours. Then the mixture is cooled and filtered. The filtrate is evaporated to dryness in vacuo at 20°–30°C. The obtained oil is treated with boiling petroleum ether to separate the insoluble product. After filtration the filtrate is evaporated to dryness. The residue is washed with water until the gamma,N'-methyl-N-piperazinopropyl chloride disappears (TLC). The oil is then dissolved in isopropanol and neutralized with HCl in isopropanol to obtain the dihydrochloride. The crystals are filtered and recrystallized from isopropanol. Yield 7.6 g, m. p. 228°C.

| Analysis for $C_{23}H_{28}N_4S.2HCl$ | C | H | N | S |
|---|---|---|---|---|
| calc. % | 59.34 | 6.49 | 12.04 | 6.87 |
| found. % | 59.04 | 6.73 | 11.63 | 7.23 |

EXAMPLE 9

2,gamma,N'-methyl-N-piperazine-n-propylthio-4-phenyl-3H-1,5-benzodiazepine monoiodomethylate (Formula I wherein R and $R^1$ = H;

$R^2$ = 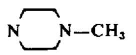

and X = $-CH_2CH_2CH_2-$)

1.42 g of methyl iodide are added to a solution cooled to 0°C of 3.92 g of 2, gamma,N'-methyl-N-piperazino-n-propylthio-4-phenyl-3H-1,5-benzodiazepine in 25 ml of acetone. The mixture is kept at 0°C for 24 hours.

Separated crystals are filtered and recrystallized from methanol. After filtration of 0.25 g of the bis-iodomethylate which is crystallized, the monoiodomethylate is obtained by concentration of the solution to a small volume. Yield 3.47 g, m. p. 167°C.

| Analysis for $C_{24}H_{31}IN_4S$ | | | | | |
|---|---|---|---|---|---|
| calc. % | 53.93 | 5.84 | 10.48 | 23.75 | 5.98 |
| found. % | 54.36 | 5.71 | 10.24 | 23.62 | 6.24 |

EXAMPLE 10

2, gamma,N'-methyl-N-piperazinpropylthio-4-phenyl-3H-1,5-benzodiazepine bis-iodomethylate (Formula I wherein R and $R^1$ = H;

$R^2$ = 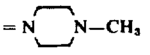

and X = $-CH_2CH_2CH_2-$)

6.39 g of methyl iodide are added to a solution of 5.88 g of 2,gamma-N'-methyl-N-piperazinopropylthio-4-phenyl-3H-1,5-benzodiazepine in 60 ml of acetone. The mixture is kept at 20°–30°C for 40 hours. It is observed that the product crystallizes. The crystals are filtered and recrystallized from methanol.

Yield 7.3 g, m. p. 226°C

| Analysis for $C_{25}H_{31}I_2N_4S$ | C | H | N | J | S |
|---|---|---|---|---|---|
| calc. % | 44.39 | 5.06 | 8.28 | 37.52 | 4.73 |
| found % | 44.66 | 5.36 | 8.34 | 38.12 | 5.06 |

EXAMPLE 11

2,gamma,N-dimethylaminopropylthio-4-phenyl-3H-1,5-benzodiazepine.HCl (Formula I wherein R and $R^1$ = H; $R^2 = N(CH_3)_2$ and X = $-CH_2-CH_2-CH_2-$)

A mixture of 5.04 g of 4-phenyl-1,3-dihydro-2H-1,5-benzodiazepine-2-thione, 1 g of 50 percent sodium hydride in oil and 400 ml of anhydrous ethyl ether is refluxed for 30 minutes, then a solution of 3.63 g of gamma,N-dimethylaminopropyl chloride in 10 ml of anhydrous ethyl ether is added dropwise in 5 minutes.

The mixture is refluxed for 10 hours. After cooling the precipitate is filtered. The filtrate is evaporated to dryness, the residue is dissolved in petroleum ether and the insoluble fraction is separated by filtration.

The solvent is evaporated in vacuo and the residue is heated to 50°/0.1 mm Hg until the excess of gamma,N-dimethylaminopropyl chloride is removed.

The oil is then dissolved in isopropanol and neutralized with HCl in isopropanol.

By cooling the hydrochloride crystallizes with one molecule of isopropyl alcohol. The crystals are recrystallized from isopropyl alcohol.

Yield 5.1 g, m. p. 80°C.

| Analysis for $C_{20}H_{23}N_3S.HCl.C_3H_8O$ | C | H | N | S | $C_3H_7O$ |
|---|---|---|---|---|---|
| calc. % | 63.65 | 7.43 | 9.68 | 7.37 | 13.61 |
| found. % | 63.68 | 7.42 | 9.60 | 7.71 | 13.42 |

EXAMPLE 12

2,gamma,N-dimethylaminopropylthio-4-phenyl-3H-1,5-benzo-diazepine iodomethylate (Formula I wherein R and $R^1$ =H; $R^2 = N(CH_3)_2$ and X = $-CH_2-CH_2-CH_2-$)

2.13 g of methyl iodide are added to a solution of 3.37 g of 2,gamma,N-dimethylaminopropylthio-4-phenyl-3H-1,5-benzodiazepine in 20 ml of acetone and the mixture is kept at 20°–30° for 60 hours. The crystals are filtered and recrystallized from isopropyl alcohol.

| Analysis for $C_{21}H_{26}N_3SI$ | C | H | N | S | I |
|---|---|---|---|---|---|
| calc. % | 52.61 | 5.34 | 8.76 | 6.67 | 26.47 |
| found % | 52.89 | 5.69 | 8.67 | 6.85 | 25.94 |

EXAMPLE 13

2,gamma,N-pyrrolidinopropylthio-4,p-chlorophenyl-3H-1,5-benzodiazepine·HCl (Formula I wherein R = H; $R^1$ = p-Cl;

$R^2 =$ 

and X = $-CH_2-CH_2-CH_2-$)

One gram of 50 percent sodium hydride in oil is added to 5.72 g of 4,p-chlorophenyl-1,3-dihydro-2H-1,5-benzodiazepine-2-thione in 400 ml of anhydrous benzene and refluxed for 30 minutes. The obtained sodium salt is refluxed for 10 hours with 4.42 g of 1,N-pyrrolidino-3-chloropropane in 15 ml of benzene. After filtration the solvent is evaporated. The excess of 1,N-pyrrolidino-3-chloropropane is removed by distillation at 60°/0.2 mm Hg in a stream of nitrogen. The residue is crystallized from petroleum ether. Yield 5.6 g, m. p. 73-74°C.

| Analysis for $C_{22}H_{24}N_3ClS$ | C | H | N | Cl | S |
|---|---|---|---|---|---|
| calc. % | 66.40 | 6.08 | 10.56 | 8.91 | 8.06 |
| found. % | 66.61 | 6.17 | 10.42 | 9.24 | 8.00 |

The hydrochloride is prepared by neutralizing with HCl in isopropanol an isopropanol solution of the base and was crystallized from isopropanol. Yield 4.35 g, m. p. 193-194°C.

| Analysis for $C_{22}H_{24}N_3ClS.HCl$ | C | H | N | Cl | S |
|---|---|---|---|---|---|
| calc. % | 60.97 | 5.81 | 9.69 | 16.38 | 7.41 |
| found. % | 60.92 | 5.48 | 9.68 | 16.57 | 7.24 |

EXAMPLE 14

2,gamma,N-pyrrolidinopropylthio-4,p-chlorophenyl-3H-1.5-benzodiazepine iodomethylate (Formula I wherein R = H; $R^1$ = p-Cl;

$R^2 =$ 

and X = $-CH_2-CH_2-CH_2-$)

0.213 g of methyl iodide are added to a solution of 0.397 g of 2,gamma-N-pyrrolidinopropylthio-4,p-chlorophenyl-3H-1.5-benzodiazepine in 20 ml of isopropanol. After 15 hours at room temperature the product crystallizes. After cooling the crystals are filtered and crystallized from ethanol. Yield 0.425 g, m. p. 156-157°C.

| Analysis for $C_{23}H_{27}N_3SClI$ | C | H | H | I | S |
|---|---|---|---|---|---|
| calc. % | 51.16 | 5.04 | 7.78 | 23.51 | 5.94 |
| found % | 51.05 | 4.70 | 7.56 | 23.35 | 6.26 |

EXAMPLE 15

2,beta,N-pyrrolidinoethylthio-4,p-chlorophenyl-3H-1,5-benzodiazepine (Formula I wherein R = H; $R^1$ = p-Cl;

$R^2 =$ 

and X = $-CH_2-CH_2-$).

2.5 g of a 50 percent oily suspension of sodium hydride is added to a solution of 8.6 g of 4,p-chlorophenyl-1,3-dihydro-2H-1,5-benzodiazepine-2-thione in 600 ml of anhydrous benzene and refluxed for 30 minutes. The obtained sodium salt is refluxed for 10 hours with 6 g of 1,N-pyrrolidino-2-chloroethane. The mixture is filtered and the solvent is evaporated. After heating for 2 hours at 60°C/0.2 mm Hg under a stream of nitrogen to remove the 1,N-pyrrolidino-2-chloroethane, the residue is crystallized from petroleum ether. Yield 8.39 g, m. p. 76°C.

| Analysis for $C_{21}H_{22}N_3ClS$ | C | H | N | Cl | S |
|---|---|---|---|---|---|
| calc. % | 65.70 | 5.77 | 10.95 | 9.24 | 8.35 |
| found % | 65.92 | 5.51 | 10.79 | 9.65 | 8.19 |

The hydrochloride is prepared by acidifying the base in an isopropanol solution and it is crystallized from isopropanol; m. p. 224°C.

| Analysis for $C_{21}H_{22}N_3SCl.HCl$ | C | H | N | Cl | S |
|---|---|---|---|---|---|
| calc. % | 60.00 | 5.51 | 9.99 | 17.26 | 7.63 |
| found % | 59.75 | 5.70 | 9.72 | 17.42 | 7.52 |

EXAMPLE 16

2,β,N-pyrrolidinoethylthio-4,p-chlorophenyl-3H-1,5-benzodiazepine iodomethylate (Formula I wherein R = H; $R^1$ = p-Cl;

$R^2 =$ 

and X = $-CH_2-CH_2-$)

0.213 g of methyl iodide are added to a solution of 0.383 g of 2,beta,N-pyrrolidinoethylthio-4,p-chlorophenyl-3H-1, 5-benzodiazepine in 20 ml of isopropanol. After about 15 hours at room temperature, an oil is separated; the solvent is decanted and a part of the product is crystallized therefrom. The oily residue is treated with isopropanol up to solidification.

After cooling and filtering the products are collected together and are crystallized from ethanol. Yield 0.6 g; m. p. 190-191°C.

| Analysis for $C_{22}H_{25}N_3SClI$ | C | H | N | I | S |
|---|---|---|---|---|---|
| calc. % | 50.24 | 4.79 | 7.99 | 24.13 | 6.09 |
| found % | 49.99 | 4.49 | 7.78 | 24.15 | 6.41 |

EXAMPLE 17

2,beta,N-diethylaminoethylthio-4,p-chlorophenyl-3H-1,5-benzodiazepine·HCl (Formula I wherein R = H; $R^1$ = p-Cl; $R^2 = N(C_2H_5)_2$ and X=$-CH_2-CH_2-$)

A mixture of 2.52 g of 4,p-chlorophenyl-1,3-dihydro-2H-1,5-benzodiazepine-2-thione, 0.50 g of 50 percent sodium hydride in oil and 200 ml of benzene is refluxed for 30 minutes, then a solution of 2.02 g of beta-diethylaminoethylchloride in 7 ml of benzene is added dropwise over 5 minutes.

The mixture is refluxed for 10 hours. After cooling the sodium chloride is filtered off. The filtrate is evaporated in vacuo at 30°C. The oily residue is dissolved in petroleum ether and a small insoluble amount of product is filtered. (0.400 g of starting product m. p. 235°C.) The solution is evaporated to dryness in vacuo. The residue is heated to 50° in vacuo to remove the excess of beta-diethylaminoethyl-chloride. The oily residue is then dissolved in isopropanol and acidifying with HCl in isopropanol. The product is crystallized by addition of anhydrous ethyl ether to the solution. Yield 3.08 g, m. p. 159°C.

| Analysis for $C_{21}H_{24}ClN_3S.HCl$ | C | H | N | S |
|---|---|---|---|---|
| calc. % | 59.71 | 5.96 | 9.94 | 7.57 |
| found % | 59.73 | 5.94 | 9.81 | 7.32 |

EXAMPLE 18

2,beta,N-diethylaminoethylthio-4,p-chlorophenyl-3H-1,5-benzodiazepine iodomethylate.

(Formula I wherein R = H; $R^1$ = p-Cl; $R^2 = N(C_2H_5)_2$ and X = $-CH_2-CH_2-$)

2.13 g of methyl iodide are added to a solution of 3.85 g of 2,beta,N-diethylaminoethylthio-4,p-chlorophenyl-3H-1,5-benzodiazepine in 35 ml of acetone. The mixture is kept at 20°–30° for 60 hours, then is cooled, filtered and crystallized from acetone. Yield 4.5 g, m. p. 182°C.

| Analysis for $C_{22}H_{27}N_3ClIS$ | C | H | N | S | I |
|---|---|---|---|---|---|
| calc. % | 50.05 | 5.15 | 7.96 | 6.06 | 24.04 |
| found % | 50.38 | 5.20 | 8.11 | 6.44 | 24.03 |

EXAMPLE 19

2,gamma,N-diethylaminopropylthio-4,p-chlorophenyl-3H-1,5-benzodiazepine·HCl (Formula I wherein R = H; $R^1$ = p-Cl; $R^2 = N(C_2H_5)_2$ and X = $-CH_2-CH_2-CH_2-$)

8.6 g of 4,p-chlorophenyl-1,3-dihydro-2H-1,5-benzodiazepine-2-thione in 600 ml of anhydrous benzene are refluxed for 30 minutes with 1.5 g of sodium hydride in a 50 percent oily suspension. To the mixture 6.2 g of 1-diethylamino-3-chloropropane is added and refluxed for 10 hours. The mixture is filtered, the solvent is evaporated and the residue is heated for 2 hours at 60°C/0.2 mm Hg in a stream of nitrogen to remove the excess of 1-diethylamino-3-chloropropane. The residue is dissolved in petroleum ether and filtered with charcoal; the solvent is evaporated and the residue is dissolved in isopropanol and neutralized with HCl in isopropanol. The hydrochloride is filtered and crystallized from ethyl acetate. Yield 8.0 g, m. p. 159-160°C.

| Analysis for $C_{22}H_{26}N_3ClS.HCl$ | C | H | N | Cl | S |
|---|---|---|---|---|---|
| calc. % | 60.55 | 6.24 | 9.63 | 16.35 | 7.53 |
| found % | 60.33 | 6.41 | 9.63 | 16.10 | 7.09 |

EXAMPLE 20

2,gamma,N-diethylaminopropylthio-4,p-chlorophenyl-3H-1,5-benzodiazepine iodomethylate (Formula I wherein R = H; $R^1$ = p-Cl; $R^2 = N(C_2H_5)_2$ and X = $-CH_2-CH_2-CH_2-$)

0.213 g of methyl iodide are added to 0.399 g of 2,gamma,N-diethylamiopropylthio-4,p-chlorophenyl-3H-1,5-benzodiazepine in 10 ml of ethanol. The mixture is kept for 4 days at room temperature. After cooling the precipitate is collected and crystallized twice from ethanol. Yield 0.26 g, m. p. 162°C.

| Analysis for $C_{23}H_{29}N_3SClI$ | C | H | N | I | S |
|---|---|---|---|---|---|
| calc. % | 50.97 | 5.39 | 7.75 | 23.42 | 5.91 |
| found % | 51.13 | 5.31 | 7.63 | 23.58 | 6.27 |

EXAMPLE 21

2,beta,N-diethylaminothylthio-4,m-chlorophenyl-3H-1,5-benzodiazepine·HCl (Formula I wherein R = H; $R^1$ = m-Cl; $R^2$ = $N(C_2H_5)_2$ and X = $-CH_2-CH_2-$)

One gram of sodium hydride in a 50 percent oily suspension is added to a solution of 5.74 g of 4,m-chlorophenyl-1,3-dihydro-2H-1,-5-benzodiazepine-2-thione (prepared in a similar way as 4,p-chlorophenyl-1,3-dihydro-2H-1,5-benzodiazepine-2-thione, Example 4) in 400 ml of benzene. To the suspension of sodium salt, obtained by refluxing for 30 minutes, 4.05 g of diethylaminochloroethane is added and refluxed for 10 hours. After filtering, the solvent is evaporated. The residue is heated for 2 hours at 60°C/0.2 mm Hg in a stream of nitrogen to remove the excess of diethylaminochloroethane. The residual oil is dissolved in petroleum ether and filtered with charcoal; the solvent is evaporated and the residue is treated with isopropyl alcohol and acidified with HCl in isopropanol. After one night at room temperature, the hydrochloride crystallizes. After cooling, the crystals are filtered and crystallized from ethyl acetate.

Yield 5.61 g, m. p. 149°–150°C.

| Analysis for $C_{21}H_{24}N_3SCl.HCl$ | C | H | N | Cl | S |
|---|---|---|---|---|---|
| calc. % | 59.71 | 5.97 | 9.95 | 16.78 | 7.59 |
| found % | 60.04 | 5.73 | 9.98 | 16.73 | 7.66 |

EXAMPLE 22

2,beta,N-diethylaminoethylthio-4,m-chlorophenyl-3H-1,5-benzodiazepine iodomethylate (Formula I wherein R = H; $R^1$ = m-Cl; $R^2$ = $N(C_2H_5)_2$ and X = $-CH_2CH_2-$)

0.213 g of methyl iodide are added at 20°C to a solution of 0.385 g of 2,beta,N-diethylaminoethylthio-4,m-chlorophenyl-3H-1,5-benzodiazepine in 4 ml of acetone. After 48 hours at 20°C, the mixture is cooled and filtered.

Yield 0.357 g; m. p. 177°–178°C. The product is crystallized from ethanol.

| Analysis for $C_{22}H_{27}N_3SCl.I$ | C | H | N | S | I |
|---|---|---|---|---|---|
| calc. % | 50.06 | 5.15 | 7.96 | 6.07 | 24.04 |
| found % | 49.90 | 4.88 | 7.78 | 6.34 | 23.88 |

EXAMPLE 23

2,beta,N-diethylaminoethylthio-4,o-chlorophenyl-3H-1,5-benzodiazepine·HCl (Formula I wherein R = H; $R^1$ = o-Cl; $R^2$ = $N(C_2H_5)_2$ and X = $-CH_2CH_2-$)

1 g of 50 percent sodium hydride in oil is added to a mixture of 5.74 g of 4,o-chlorophenyl-1,3-dihydro-2H-1,5-benzodiazepine-2-thione (prepared in a similar way as 4,p-chlorophenyl-1,3-dihydro-2H-1,5-benzodiazepine-2-thione, Example 4) in 400 ml of anhydrous benzene. After refluxing for one hour, a solution of 4.05 g of beta-diethylaminoethylchloride in 15 ml of benzene is added to the mixture and refluxed for 10 hours.

After filtering, the solvent is evaporated and the excess of beta-diethylaminoethylchloride is removed by heating for 2 hours at 60°C/0.05 mm Hg in a stream of nitrogen.

The residue is dissolved in petroleum ether, treated with charcoal and filtered. The solvent is evaporated and the residue is treated with isopropanol and weakly acidified with HCl in isopropanol. The hydrochloride is filtered and crystallized from isopropanol. Yield 5.2 g, m. p. 175°C.

| Analysis for $C_{21}H_{24}N_3SCl.HCl$ | C | H | N | Cl | S |
|---|---|---|---|---|---|
| calc. % | 59.71 | 5.97 | 9.95 | 16.79 | 7.59 |
| found % | 60.00 | 5.83 | 9.84 | 16.51 | 7.87 |

EXAMPLE 24

2,β,N-diethylaminoethylthio-4,o-chlorophenyl-3H-1,5-benzodiazepine iodomethylate (Formula I wherein R = H; $R^1$ = o-Cl; $R^2$ = $N(C_2H_5)_2$ and X = $-CH_2CH_2-$)

0.213 g of methyl iodide are added at room temperature to a solution of 0.385 g of 2,beta,N-diethylaminoethylthio-4,-o-chlorophenyl-3H-1.5-benzodiazepine in 20 ml of isopropanol. After 15 hours at 20°, the product crystallizes. It is filtered and re-crystallized from ethanol.

Yield 0.35 g, m. p. 192°–193°C.

| Analysis for $C_{22}H_{27}N_3SCl.I$ | C | H | N | S | I |
|---|---|---|---|---|---|
| calc. % | 50.06 | 5.15 | 7.96 | 6.07 | 24.04 |
| found % | 49.99 | 5.40 | 7.74 | 6.42 | 24.27 |

EXAMPLE 25

2,beta-N-diethylaminoethylthio-4,p-diphenylyl-3H-1,5-benzodiazepine.HCl (Formula I wherein R = H; $R^1$ = p-$C_6H_5$; $R^2$ = $N(C_2H_5)_2$ and X = $-CH_2CH_2-$)

A mixture of 3.28 g of 4,p-diphenylyl-1,3-dihydro-2H-1,5-benzodiazepine-2-thione, 0.50 g of 50 percent sodium hydride in oil and 200 ml of benzene are refluxed for 30 minutes, then a solution of 2.02 g of beta-diethylaminoethyl chloride in 7 ml of benzene is added dropwise over 5 minutes. The mixture is refluxed for 10 hours. Then the mixture is cooled and the sodium chloride is filtered off. The filtrate is evaporated to dryness in vacuo at 20°–30°C. The oily residue is dissolved in petroleum ether and the insoluble product is filtered off. (1.1 g of starting product m. p. 232°C).

The filtrate is evaporated to dryness in vacuo at 20°–30°C. The residue is heated to 50° in vacuo (0.01 mm Hg) to remove the excess of beta-diethylaminoethyl chloride. This treatment is continued until the beta-diethylaminoethyl chloride disappears (TLC). The oil is then dissolved in isopropanol and weakly acidified with HCl in isopropanol.

The product crystallizes by addition of anhydrous ethyl ether to the solution.

Yield 2.8 g, m. p. 168°–169°C.

| Analysis for $C_{27}H_{29}N_3S.HCl$ | C | H | N | S |
|---|---|---|---|---|
| calc. % | 69.88 | 6.51 | 9.05 | 6.89 |
| found % | 69.36 | 6.66 | 9.19 | 7.10 |

EXAMPLE 26

2,beta,N-diethylaminoethylthio-4-diphenylyl-3H-1,5-benzodiazepine iodomethylate (Formula I wherein R = H; $R^1$ = p-$C_6H_5$; $R^2$ = $N(C_2H_5)_2$ and X = $-CH_2CH_2-$)

2.13 g of methyl iodide is added to a solution of 4.27 g of 2,beta,N-diethylaminoethylthio-4-diphenylyl-3H-1,5-benzodiazepine in 60 ml of acetone. The mixture is kept at 20°–30° for 60 hours.

The crystals are filtered and recrystallized from methanol. Yield 4.75 g, m. p. 203°–204°C.

| Analysis for $C_{28}H_{32}N_3IS$ | C | H | N | I | S |
|---|---|---|---|---|---|
| calc. % | 59.04 | 5.66 | 7.37 | 22.28 | 5.61 |
| found % | 58.84 | 5.66 | 6.90 | 22.05 | 5.62 |

EXAMPLE 27

2,beta,N-diethylaminoethylthio-4,p-phenoxyphenyl-3H-1,5-benzodiazepine.HCl (Formula I wherein R = H; $R^1$ = p-$C_6H_5O$; $R^2$ = $N(C_2H_5)_2$ and X = $-CH_2CH_2-$)

A mixture of 3.44 g of 4,p-phenoxyphenyl-1,3-dihydro-2H-1,5-benzodiazepine-2-thione, 0.50 g of 50 percent sodium hydride in oil and 200 ml of benzene is refluxed for 30 minutes, then a solution a 2.02 g of beta-diethylaminoethyl chloride in 7 ml of benzene is added dropwise in 5 minutes.

The mixture is refluxed for 10 hours. The mixture is then cooled and the sodium chloride is filtered off. The filtrate is evaporated to dryness in vacuo at 20°–30°C. The oily residue is dissolved in petroleum ether and the solution is filtered with charcoal.

The solvent is evaporated in vacuo and the residue is heated to 50° at 0.01 mm Hg to remove the excess of β-diethylaminoethyl chloride. This treatment is continued until the betadiethylaminoethyl chloride disappears (TLC). The oil is then dissolved in isopropanol and weakly acidified with HCl in isopropanol. The product crystallizes by addition of anhydrous ethyl ether to the solution and the crystals are collected. Yield 9.15 g, m. p. 149°C.

| Analysis for $C_{27}H_{29}N_3OS.HCl$ | C | H | N | S |
|---|---|---|---|---|
| calc. % | 67.55 | 6.30 | 8.75 | 6.66 |
| found % | 67.85 | 5.87 | 9.05 | 6.33 |

EXAMPLE 28

2,beta,N-diethylaminoethylthio-4,p-phenoxyphenyl-3H-1,5-benzodiazepine iodomethylate (Formula I wherein R = H; $R^1$ = p-$C_6H_5O$; $R^2$ = $N(C_2H_5)_2$ and X = $-CH_2CH_2-$)

2.13 g of methyl iodide are added to a solution of 4.43 g of 2,beta,N-diethylaminoethylthio-4,p-phenoxyphenyl-3H-1,5-benzodiazepine in 40 ml of acetone. The mixture is kept at 20°–30° for 60 hours. The crystals are filtered and recrystallized from ethanol.

Yield 4.5 g, m. p. 180°C.

| Analysis for $C_{28}H_{32}N_3OS.I$ | C | H | N | I | S |
|---|---|---|---|---|---|
| calc. % | 57.43 | 5.48 | 7.17 | 21.68 | 5.46 |
| found % | 57.15 | 5.50 | 7.37 | 22.38 | 5.64 |

EXAMPLE 29

2,beta-N-diethylaminoethylthio-4,p-phenylthiophenyl-3H-1,5-benzodiazepine.HOl (Formula I wherein R = H; $R^1$ = p-$C_6H_5S$-;$R^2$ = $N(C_2H_5)_2$ and X = $-CH_2CH_2-$)

A mixture of 3.6 g of 4,p-phenylthiophenyl-1,3-dihydro-2H-1,5-benzodiazepine-2-thione, 0.50 g of 50 percent sodium hydride in oil and 200 ml of benzene is refluxed for 30 minutes, then a solution of 2.02 g of beta-diethylaminoethyl chloride in 5 ml of benzene are added dropwise over 5 minutes.

The mixture is refluxed for 10 hours. The mixture is then cooled and filtered to separate the sodium chloride. The filtrate is evaporated to dryness in vacuo. The oily residue is dissolved in petroleum ether and the solution is filtered with charcoal. The solvent is evaporated in vacuo. The oily residue is heated to 50° in vacuo (0.01 mm Hg) to remove the excess of beta-diethylaminoethyl chloride. This treatment is continued until the beta-diethylaminoethyl chloride disappears (TLC). The oil is then dissolved in isopropanol and weakly acidified with HCl in propanol. The product crystallizes by addition of anhydrous ethyl ether to the solution. The crystals are filtered and recrystallized from ethyl acetate. Yield 3.65 g, m. p. 150°C.

| Analysis for $C_{27}H_{29}N_3S_2.HCl$ | C | H | N | S |
|---|---|---|---|---|
| calc. % | 65.36 | 6.09 | 8.47 | 12.90 |
| found % | 65.18 | 6.40 | 8.52 | 12.85 |

EXAMPLE 30

2,beta,N-diethylaminoethylthio-4,p-phenylthio-phenyl-3H-1,5-benzodiazepine iodomethylate (Formula I wherein R = H; $R^1$ = p-$C_6H_5S$-; $R^2$ = $N(C_2H_5)_2$ and X = $-CH_2-CH_2-$)

2.55 g of methyl iodide are added to a solution of 5.93 g of 2,beta,N-diethylaminoethylthio-4-p-phenylthiophenyl-3H-1,5-benzodiazepine in 100 ml of isopropanol. The mixture is kept at 20°–30° for 60 hours. The crystals are then filtered. Yield 6.2 g, m. p. 161°C.

| Analysis for $C_{28}H_{32}N_3S_2.I$ | C | H | N | I | S |
|---|---|---|---|---|---|
| calc. % | 55.90 | 5.36 | 6.98 | 21.10 | 10.64 |
| found % | 55.72 | 5.29 | 7.11 | 21.27 | 10.73 |

EXAMPLE 31

2,beta,N-diethylaminoethylthio-4,p-phenylthio-phenyl-3H-1,5-benzodiazepine bromobenzylate (Formula I wherein R = H; $R^1$ - p-$C_6H_5$S-; $R^2$ = N($C_2H_5$)$_2$ and X = -$CH_2$-$CH_2$-)

0.427 g of benzyl bromide is added to a solution of 0.918 g of 2, beta,N-diethylaminoethylthio-4,p-phenylthiophenyl-3H-1,5-benzodiazepine in 20 ml of isopropanol and the mixture is kept at 20°–25° for 4 days. It is then filtered and crystallized from isopropanol. Yield 0.8 g, m. p. 134°C.

| Analysis for $C_{34}H_{36}N_3S_2Br$ | | | | |
|---|---|---|---|---|
| | C | H | N | S |
| calc. % | 64.74 | 5.75 | 6.66 | 10.17 |
| found % | 64.71 | 5.94 | 6.77 | 10.21 |

EXAMPLE 32

2,beta,N-diethylaminoethylthio-4,p-phenylthiophenyl-3H-1,5-benzodiazepine methyl nitrate (Formula I wherein R = H; $R^1$ = p-$C_6H_5$S-; $R^2$ = N($C_2H_5$)$_2$ and X = -$CH_2CH_2$-)

a. A solution of 0.601 g of 2,beta,N-diethylaminoethylthio-4,p-phenylthiophenyl-3H-1,5-benzodiazepine iodomethylate in 6 ml of methanol is added at 25°C to a solution of 0.16 g of silver nitrate in 8.5 ml of methanol.

The precipitated silver iodide is filtered, methanol is evaporated, the residue is treated with ethyl acetate, the white solid precipitate is collected and crystallized from isopropanol. Yield 0.46 g, m. p. 149°C.

b. A 0.5 N NaOH solution is passed through a column of 10 ml of Amberlite IRA 400 resin, until the collected solution shows the same normality as the solution poured into the column. The column is then washed till the washing waters are neutral. Then, a solution of 1.2 g of 2,beta,N-diethylaminoethylthio-4,p-phenylthiophenyl-3H-1,5-benzodiazepine iodomethylate in 80 ml of ethanol and 20 ml of water is passed in 3 hours and the eluate is collected in a flask cooled with ice. A sample of the collected solution containing the 2,beta,N-methyldiethylammoniumethylthio-4, p-phenylthiophenyl-3H-1,5-benzodiazepine hydroxide is titrated with 0.01 N HCl : 85 percent of the theoretical yield is found.

The remaining solution is then neutralized with the theoretical quantity of nitric acid, evaporated to dryness and the oily residue is treated with ethyl acetate. A white product is obtained which is crystallized from isopropanol: theoretical yield calculated on 2,beta,N-methyldiethylammoniumethylthio-4,p-phenylthiophenyl- 3H-1,5-benzodiazepine hydroxide. m p. 148°–149°C.

| Analysis for $C_{28}H_{32}N_4S_2O_3$ | | | |
|---|---|---|---|
| | C | H | N |
| calc. % | 62.66 | 6.01 | 10.44 |
| found % | 62.39 | 5.74 | 10.30 |

EXAMPLE 33

2,beta-methyldiethylammoniumethylthio-4,p-phenylthiophenyl-3H-1,5-benzodiazepine tartrate hydrated (Formula I wherein R = H; $R^1$ = p-$C_6H_5$S-; $R^2$ = N($C_2H_5$)$_2$ and X = -$CH_2CH_2$-)

A 0.5 N NaOH solution is passed through a column of 10 ml of Amberlite IRA 400 resin until the collected solution shows the same normality as the solution poured into the column. The column is then washed till the washing waters are neutral. Then, a solution of 1.2 g of 2,beta-diethylaminoethylthio-4,p-phenyl-thiophenyl-3H-1,5-benzodiazepine iodomethylate in 80 ml of ethanol and 20 ml of water is passed in about 3 hours and the eluate is collected in a flask cooled with ice. A sample of the collected solution, containing the 2,beta,-methyldiethylammoniumethylthio-4,p-phenylthiophenyl-3H-1,5-benzodiazepine hydroxide is titrated with 0.01 N HCl : 85 percent of the theoretical yield is found. The theoretical quantity of d,l-tartaric acid is then added to the eluate and the solution is kept at 20°–30°C for 24 hours. It is then evaporated to dryness and the residue is crystallized from isopropanol. Yield 0.820 g, m. p. 58-62°C.

| Analysis for $C_{28}H_{32}N_3S_2 \cdot C_4H_5O_6 \cdot H_2O$ | | | |
|---|---|---|---|
| | C | H | N | S |
| calc. % | 59.88 | 6.11 | 6.53 | 9.94 |
| found % | 60.09 | 5.92 | 6.47 | 10.12 |

EXAMPLE 34

2,beta,N(N'-methyl)piperazinoethylthio-4,p-phenylthiophenyl-3H-1,5-benzodiazepine citrate (Formula I wherein R = H; $R^1$ = p-$C_6H_5$S-;

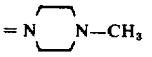

and X = -$CH_2CH_2$-)

A solution of 3.6 g of 4,p-phenylthiophenyl-1,3-dihydro-2H-1,5-benzodiazepine-2-thione in 200 ml of anhydrous benzene is refluxed for 30 minutes with 0.5 g of a 50 percent oily suspension of sodium hydride. A solution of 2.47 g of 2(N'-methyl)-N-piperazino-1-chloroethane in 8 ml of anhydrous benzene is then added dropwise in 10 minutes and the mixture is refluxed for 10 hours. After filtration, the solvent is evaporated and the residual oil is crystallized from petroleum ether. Yield 3.5 g of 2,beta,N-(N'-methyl)-piperazinoethylthio-4,p-phenylthiophenyl-3H-1,5-benzodiazepine m. p. 85°C.

| Analysis for $C_{28}H_{30}N_4S_2$ | | | | |
|---|---|---|---|---|
| | C | H | N | S |
| calc. % | 69.12 | 6.22 | 11.51 | 13.18 |
| found % | 68.90 | 6.51 | 11.46 | 13.03 |

To a solution of 4.86 g, of 2,beta,N-(N'-methyl)-piperazinoethylthio-4,p-phenylthiophenyl-3H-1,5-benzodiazepine in 80 ml of isopropanol 1.92 g of citric acid are added and the mixture is heated until a solution is obtained. The citrate is crystallized by cooling and is then recrystallized from ethanol. Yield 5.5 g, m. p. 174°C.

| Analysis for $C_{28}H_{30}N_4S_2.C_6H_8O_7$ | C | H | N |
|---|---|---|---|
| calc. % | 60.16 | 5.66 | 8.25 |
| found % | 59.96 | 5.88 | 8.69 |

EXAMPLE 35

2,beta,N(N'-methyl)piperazinoethylthio-4,p-phenylthiophenyl-3H-1,5-benzodiazepine monoiodomethylate (Formula I wherein R = H; $R^1$ = p-$C_6H_5S$-;

$R^2$ = 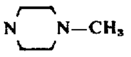

and X = -$CH_2CH_2$-)

0.14 g of methyl iodide are added at room temperature to a solution of 0.486 g of 2,beta,N(N'-methyl)-piperazinoethylthio-4,p-phenylthiophenyl-3H-1,5-benzodiazepine in 15 ml of isopropanol. After keeping for 4 days at room temperature, the mixture is filtered. Yield 0.58 g, m. p. 185°C.

| Analysis for $C_{29}H_{33}N_4S_2J$ | C | H | N | I | S |
|---|---|---|---|---|---|
| calc. % | 55.41 | 5.29 | 8.91 | 20.19 | 10.20 |
| found % | 55.15 | 5.53 | 8.64 | 19.97 | 9.92 |

EXAMPLE 36

2,beta,N(N'-methyl)piperazinoethylthio-4-p-phenylthiophenyl-3H-1,5-benzodiazepine bis-iodomethylate (Formula I wherein R = H; $R^1$ = p-$C_6H_5S$-;

$R^2$ = 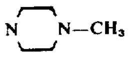

and X = -$CH_2CH_2$-)

0.426 g of methyliodide is added at room temperature to a solution of 0.486 g of 2,beta,N(N'-methyl)-piperazinoethylthio-4,p-phenylthiophenyl-3H-1,5-benzodiazepine in 15 ml of acetone. After keeping for 4 days at room temperature, the mixture is cooled, filtered and crystallized from aqueous ethanol. Yield 0.5 g; m. p. 177°C.

| Analysis for $C_{30}H_{36}N_4S_2I_2$ | C | H | N | I | S |
|---|---|---|---|---|---|
| calc. % | 46.76 | 4.71 | 7.27 | 32.94 | 8.32 |
| found % | 46.86 | 4.85 | 7.09 | 33.10 | 8.32 |

EXAMPLE 37

2,gamma,pyrrolidinopropylthio-4,p-phenylthiophenyl-3H-1,5-benzodiazepine.HCl (Formula I wherein R = H; $R^1$ = $C_6H_5S$-;

$R^2$ = 

and X = -$CH_2CH_2CH_2$-)

1 g of 50 percent oily suspension of sodium hydride is added to 7.2 g of 4,p-phenylthiophenyl-1,3-dihydro-2H-1,5-benzodiazepine-2-thione in 400 ml of anhydrous benzene and refluxed for 30 minutes. 4.42 g of 1,N-pyrrolidino-3-chloropropane in 15 ml of benzene is then added to the mixture and refluxed for 10 hours. It is filtered and the solvent is evaporated. The residue is heated for 2 hours at 60°C/0.2 mm Hg in a stream of nitrogen to remove the traces of 1,N-pyrrolidino-3-chloropropane. The oily residue is dissolved in petroleum ether and filtered with charcoal; the solvent is evaporated again and the residue is treated with isopropanol, and slightly acidified with HCl in isopropyl alcohol. The hydrochloride is separated by addition of ethyl ether and is crystallized from isopropanol. Yield 5.6 g; m. p. 176°C.

| Analysis for $C_{28}H_{29}N_3S_2.HCl$ | C | H | N | Cl | S |
|---|---|---|---|---|---|
| calc. % | 66.19 | 5.95 | 8.27 | 6.98 | 12.61 |
| found % | 65.92 | 6.00 | 8.15 | 7.33 | 12.51 |

EXAMPLE 38

2,gamma,N-pyrrolidinopropylthio-4,p-phenylthiophenyl-3H-1,5-benzodiazepine iodomethylate (Formula I wherein R = H; $R^1$ = p-$C_6H_5S$-;

$R^2$ = 

and X = -$CH_2CH_2CH_2$-)

0.213 g of methyl iodide is added to 0.471 g of 2,gamma,N-pyrrolidinopropylthio-4,p-phenylthiophenyl-3H-1,5-benzodiazepine in 10 ml of isopropanol and the mixture is kept for 15 hours at room temperature. At the end, an oil separates and the product crystallizes from the decanted solvent. The oil treated with isopropanol solidifies and is filtered. The combined products are crystallized from ethanol. Yield 0.32 g; m. p. 190-191°C.

| Analysis for $C_{29}H_{32}N_3S_2I$ | C | H | N | S | I |
|---|---|---|---|---|---|
| calc. % | 56.76 | 5.25 | 6.85 | 10.45 | 20.68 |
| found % | 56.90 | 5.14 | 6.72 | 10.25 | 20.43 |

EXAMPLE 39

2,gamma,N-diethylaminopropylthio-4,p-phenylthiophenyl-3H-1,5-benzodiazepine citrate (Formula I wherein R = H; $R^1$ = p-$C_6H_5S$-; $R^2$ = $N(C_2H_5)_2$ and X = -$CH_2CH_2CH_2$-)

0.5 g of a 50 percent sodium hydride suspension in oil are added to a solution of 3.6 g of 4,p-phenylthiophenyl-1,3-dihydro-2H-1,5-benzodiazepine-2-thione in 200 ml of benzene, and refluxed for 30 minutes. The mixture is refluxed with 2.02 g of 1-chloro-3-diethylaminopropane for 10 hours. The solvent is evaporated, and the residue is heated for 2 hours at 65°C/0.2 mm Hg. The residue is purified again by countercurrent repartition using n-butanol-water. The separation is controlled by TLC on silica gel using as a solvent butanol saturated with water and acetic acid and revealing the spots with K iodobismuthate. The fractions containing the pure product are evaporated in vacuo. To solution of this residue in 120 ml of isopropanol, 1.92 g of citric acid is added and refluxed for 10 minutes. After cooling, an oil is separated which is crystallized from ethyl acetate. A further quantity of product is separated from isopropanol solution by further cooling, crystallized from ethyl acetate and combined to the first portion. Total yield 4.3 g, m. p. 114°–115°C.

| Analysis for $C_{28}H_{31}N_3S_2.C_6H_8O_7$ | C | H | N | S |
|---|---|---|---|---|
| calc. % | 61.33 | 5.90 | 6.31 | 9.63 |
| found % | 61.05 | 5.55 | 6.27 | 9.78 |

EXAMPLE 40

2,gamma,N-diethylaminopropylthio-4,p-phenylthiophenyl-3H-1,5-benzodiazepine iodomethylate (Formula I wherein R = H; $R^1$ = p-$C_6H_5S$-; $R^2$ = $N(C_2H_5)_2$ and X = -$CH_2CH_2CH_2$-)

A solution of 2.4 g of 2,gamma,N-diethylaminopropylthio-4,p-phenylthiophenyl-3H-1,5-benzodiazepine in 80 ml of acetone and 1.06 g of methyl iodide is kept four days at 2°–25°C. After cooling, the mixture is filtered. Yield 2.15 g, m. p. 174°C. The substance crystallizes from anhydrous ethanol.

| Analysis for $C_{29}H_{34}N_3S_2I$ | C | H | N | S | I |
|---|---|---|---|---|---|
| calc. % | 56.58 | 5.57 | 6.83 | 10.42 | 20.62 |
| found % | 56.73 | 5.95 | 6.80 | 10.65 | 20.89 |

EXAMPLE 41

2,gamma,N-dimethylaminopropylthio-4,p-phenylthiophenyl-3H-1,5-benzodiazepine.HCl (Formula I wherein R = H; $R^1$ = p-$C_6H_5S$-; $R^2$ = $N(CH_3)_2$ and X = -$CH_2CH_2CH_2$-)

A solution of 3.6 g of 4,p-phenylthiophenyl-1,3-dihydro-2H-1,5-benzodiazepine-2-thione in 200 ml of anhydrous benzene is refluxed for 30 minutes with 0.5 g of a 50 percent sodium hydride oily suspension. A solution of 1.824 g of gamma-dimethylaminopropyl chloride in 7 ml of benzene is then added and the mixture is refluxed for 10 hours. The hot solution is filtered, the solvent is evaporated and the residual oil is heated for 2 hours at 65°C/0.2 mm Hg to remove the excess of gamma-dimethylaminopropyl chloride. The residue is extracted with petroleum ether, removing the less soluble product. The solvent is evaporated, the residue is treated with isopropyl alcohol and the solution slightly acidified with HCl in isopropanol. The hydrochloride is separated by addition of ethyl ether and crystallized from isopropanol. Yield 2.75 g, m. p. 111°–112°C.

| Analysis for $C_{26}H_{27}N_3S_2.HCl$ | C | H | N | Cl | S |
|---|---|---|---|---|---|
| calc. % | 64.77 | 5.85 | 8.72 | 7.35 | 13.30 |
| found % | 64.43 | 6.11 | 8.56 | 7.43 | 13.11 |

EXAMPLE 42

2,gamma,N-dimethylaminopropylthio-4,p-phenylthiophenyl-3H-1,5-benzodiazepine iodomethylate (Formula I wherein R = H; $R^1$ = p-$C_6H_5S$-; $R^2$ = $N(CH_3)_2$ and X = -$CH_2CH_2CH_2$-)

A solution of 2.34 g of 2,gamma,N-dimethylaminopropylthio-4,p-phenylthiophenyl-3H-1,5-benzodiazepine in 20 ml of acetone and 1.06 g of methyl iodide is kept for 4 days at 20°–25°C. The mixture is cooled, the separated crystals are filtered and recrystallized from ethanol. Yield 2.59 g, m. p. 200°C.

| Analysis for $C_{27}H_{30}N_3S_2I$ | C | H | N | S | I |
|---|---|---|---|---|---|
| calc. % | 55.19 | 5.15 | 7.15 | 10.91 | 21.60 |
| found % | 54.81 | 5.33 | 6.93 | 10.74 | 22.00 |

EXAMPLE 43

2,beta,N-pyrrolidinoethylthio-4,p-phenylthiophenyl-3H-1,5-benzodiazepine (Formula I wherein R = H; $R^1$= p-$C_6H_5S$-;

$R^2$ = 

and X = -$CH_2CH_2$-)

0.5 g of a 50 percent sodium hydride oily suspension is added to a solution of 3.6 g of 4,p-phenylthiophenyl-1,3-dihydro-2H-1,5-benzodiazepine-2-thione in 200 ml of anhydrous benzene and refluxed for 30 minutes. To this mixture, a solution of 2 g of beta-pyrrolidinoethyl chloride in 7 ml of benzene is added, refluxed for 10 hours and filtered. The solvent is evaporated and the excess of beta-pyrrolidinoethyl chloride is removed by heating for 2 hours at 60°C/1 mm Hg. The residual oil is crystallized from petroleum ether and filtered. Yield 3.4 g, m. p. 82°C.

| Analysis for $C_{27}H_{27}N_3S_2$ | C | H | N |
|---|---|---|---|
| calc. % | 70.86 | 5.95 | 9.18 |
| found % | 70.56 | 6.04 | 9.31 |

EXAMPLE 44

2,beta,N-pyrrolidinoethylthio-4,p-phenylthiophenyl-3H-1,5-benzodiazepine iodomethylate (Formula I wherein R = H; $R^1$ = p-$C_6H_5S$-;

$R^2$ = 

and X = -$CH_2CH_2$-)

A solution of 2.3 g of 2,beta,N-pyrrolidinoethylthio-4,p-phenylthiophenyl-3H-1,5-benzodiazepine in 12 ml of acetone and 1.06 g of methyl iodide is kept for four days at 20°–25°C. After cooling, the mixture is filtered and crystallized from 95 percent ethanol. Yield 2.2 g, m. p. 191°C.

| Analysis for $C_{28}H_{30}N_3S_2I$ | C | H | N | S | I |
|---|---|---|---|---|---|
| calc. % | 56.08 | 5.04 | 7.01 | 10.70 | 21.17 |
| found % | 56.15 | 5.15 | 6.76 | 10.47 | 21.49 |

EXAMPLE 45

2,beta,N-dimethylaminoethylthio-4,p-phenylthiophenyl-3H-1,5-benzodiazepine citrate (Formula I wherein R = H; $R^1$ = P-$C_6H_5S$-; $R^2$ = $N(CH_3)_2$ and X = -$CH_2CH_2$-)

0.5 g of a 50 percent sodium hydride oily suspension are added to a solution of 3.6 g of 4,p-phenylthiophenyl-1,3-dihydro-2H-1,5-bensodiazepine-2-thione in 200 ml of anhydrous benzene and refluxed for 30 minutes. A solution of 1.61 g of beta-dimethyl-aminoethyl chloride in 7 ml of benzene is added, the mixture is refluxed for 10 hours and filtered. The solvent is evaporated, and the excess of beta-dimethylaminoethyl chloride is removed by heating for 2 hours at 65°C/0.2 mm Hg. The residual oil is extracted with cold petroleum ether, removing the less soluble product. The solvent is evaporated and to a solution of the residue in 240 ml of hot isopropanol, 1.92 g of citric acid are added. After one night at room temperature, the mixture is cooled and filtered and then crystallized from isopropanol. Yield 3.66 g, m. p. 78°C.

| Analysis for $C_{23}H_{23}N_3S_2.C_6H_8O_7$ | C | H | N | S |
|---|---|---|---|---|
| calc. % | 59.69 | 5.33 | 6.74 | 10.38 |
| found % | 59.63 | 5.63 | 6.46 | 10.09 |

EXAMPLE 46

2,beta,N-dimethylaminoethylthio-4,p-phenylthiophenyl-3H-1,5-benzodiazepine iodomethylate (Formula I wherein R = H; $R^1$ = p-$C_6H_5S$; $R^2$ = $N(CH_3)_2$ and X = -$CH_2CH_2$-)

1.06 g of methyl iodide is added to a solution of 2.16 g of 2,beta,N-dimethylaminoethylthio-4,p-phenylthiophenyl-3H-1,5-benzodiazepine in 80 ml of isopropanol and kept for 4 days at 20°–25°C. After cooling, the mixture is filtered. Yield 2.3 g, m. p. 200°C. The substance crystallizes from ethanol.

| Analysis for $C_{24}H_{26}N_3S_2I$ | C | H | N | S | I |
|---|---|---|---|---|---|
| calc. % | 54.45 | 4.92 | 7.33 | 11.18 | 22.13 |
| found % | 54.34 | 5.06 | 7.31 | 11.31 | 22.48 |

EXAMPLE 47

2,beta,N-piperidinoethylthio-4,p-phenylthiophenyl-3H-1,5-benzodiazepine (Formula I wherein R = H; $R^1$ = p-$C_6H_5S$-;

$R^2$ = 

and X = -$CH_2CH_2$-)

A solution of 3.6 g of 4,p-phenylthiophenyl-1,3-dihydro-2H-1,5-benzodiazepine-2-thione in 200 ml of anhydrous benzene and 0.5 g of a 50 percent sodium hydride oily suspension is refluxed for 30 minutes. To this mixture a solution of 2.015 g of beta,N-piperidinoethylchloride in 7 ml of benzene is added, refluxed for 10 hours and filtered. The solvent is evaporated and the residual oil is heated for 2 hours at 65°C/0.2 mm Hg to remove the excess of beta,N-piperidinoethyl chloride. The residue is crystallized from ligroine. Yield 3.4 g, m. p. 78°C.

| Analysis for $C_{26}H_{25}N_3S_2$ | C | H | N | S |
|---|---|---|---|---|
| calc. % | 71.29 | 6.20 | 8.91 | 13.60 |
| found % | 71.45 | 6.34 | 8.91 | 13.80 |

The hydrochloride is prepared by slightly acidifying with HCl an isopropanol solution of the base. The substance crystallizes from isopropyl alcohol; m. p. 144°–145°C.

| Analysis for $C_{26}H_{29}N_3S_2.HCl.H_2O$ | C | H | N | Cl | S | $H_2O$ |
|---|---|---|---|---|---|---|
| calc. % | 63.92 | 6.13 | 7.99 | 6.74 | 12.19 | 3.42 |
| found % | 64.09 | 6.60 | 7.76 | 6.74 | 11.98 | 3.33 |

EXAMPLE 48

2,beta,N-piperidinoethylthio-4,p-phenylthiophenyl-3H-1,5-benzodiazepine iodomethylate (Formula I wherein R = H; $R^1$ = p-$C_6H_5S$-;

$R^2$ = 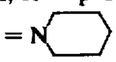

and X = -$CH_2CH_2$-)

3.5 g of methyl iodide are added to a solution of 1.97 g of 2,beta-N-piperidinoethylthio-4,p-phenylthiophenyl-3H-1,5-benzodiazepine in 64 ml of acetone and the solution is kept for 4 days at 20°–25°C. After cooling, the mixture is filtered.

Yield 1.9 g, m. p. 180°C. The substance crystallizes from ethanol.

| Analysis for $C_{26}H_{32}N_3S_2I$ | C | H | N | S | I |
|---|---|---|---|---|---|
| calc. % | 56.71 | 5.25 | 6.84 | 10.44 | 20.66 |
| found % | 56.82 | 5.51 | 6.78 | 10.14 | 21.02 |

EXAMPLE 49

2,beta,N-morpholinoethylthio-4,p-phenylthiophenyl-3H-1,5-benzodiazepine.HCl (Formula I wherein R = H; $R^1$ = p-$C_6H_5S$-;

$R^2$ = 

and X = -$CH_2CH_2$-)

A solution of 3.6 g of 4,p-phenylthiophenyl-1,3-dihydro-2H-1,5-benzodiazepine -2-thione in 200 ml of anhydrous ether and 0.5 g of sodium hydride is refluxed for 30 minutes. A solution of 2.245 g of beta,N-morpholinoethyl chloride in 7 ml of ethyl ether is added and refluxed for 10 hours. The hot solution is filtered, and the solvent is evaporated, and the traces of beta,N-morpholinoethyl chloride are removed by heating for 2 hours at 65°C/0.2 mm Hg. The residue is dissolved in 160 ml isopropanol and slightly acidified with HCl in isopropanol. The precipitate is crystallized from isopropyl alcohol. Yield 3.7 g, m. p. 215°C.

| Analysis for $C_{27}H_{27}N_3OS_2.HCl$ | C | H | N | Cl | S |
|---|---|---|---|---|---|
| calc. % | 63.57 | 5.53 | 8.23 | 6.95 | 12.57 |
| found % | 63.77 | 5.77 | 8.26 | 7.30 | 12.24 |

EXAMPLE 50

2,beta,N-morpholinoethylthio-4,p-phenylthiophenyl-3H-1,5-benzodiazepine iodomethylate (Formula I wherein R = H; $R^1$ = p-$C_6H_5S$-:

$R^2$ = 

and X = -$CH_2CH_2$-)

A solution of 2.36 g of 2,beta,N-morpholinoethylthio-4,-p-phenylthiophenyl-3H-1,5-benzodiazepine in 120 ml of acetone and 1.06 g of methyl iodide is kept at 20°–25°C for four days. After cooling, the mixture is filtered.

Yield 2.52 g, m. p. 173°C. The substance crystallizes from ethanol.

| Analysis for $C_{28}H_{30}N_3S_2OI$ | C | H | N | S | I |
|---|---|---|---|---|---|
| calc. % | 54.63 | 4.91 | 6.83 | 10.42 | 20.62 |
| found % | 54.48 | 5.08 | 6.44 | 10.38 | 21.07 |

EXAMPLE 51

2(alpha-methyl-beta-diethylamino)ethylthio-4,p-phenylthiophenyl-3H-1,5-benzodiazepine citrate (Formula I wherein R = H; $R^1$ = p-$C_6H_5S$-; $R^2$ = $N(C_2H_5)_2$ and X = 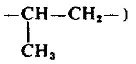

1 g of NaH in a 50 percent oily suspension is added to a solution of 7.2 g of 4,p-phenylthiophenyl-1,3-dihydro-2H-1,5-benzodiazepine-2-thione in 400 ml of anhydrous benzene and refluxed for 30 minutes. To the mixture 4.5 g of 1-diethylamino-2-chloropropane is added, refluxed for 10 hours and filtered. The solvent is evaporated and the residue is heated for 2 hours at 60°C/0.2 mm Hg in a stream of nitrogen to remove the traces of 1-diethylamino-2-chloropropane. The residue is dissolved in petroleum ether and filtered with charcoal; the solvent is evaporated, the residue is dissolved in hot isopropanol and 3.84 g of citric acid are added to the solution. After one night at room temperature, an oil is separated, the liquid is decanted, evaporated to dryness, and crystallized from ethyl acetate. The oil is dissolved and crystallized from ethyl acetate. The products are collected together and recrystallized from ethyl acetate. Yield 7 g, m. p. 138° C.

| Analysis for $C_{28}H_{31}N_3S_2.C_6H_8O_7$ | C | H | N | S |
|---|---|---|---|---|
| calc. % | 61.33 | 5.90 | 6.31 | 9.48 |
| found % | 61.01 | 5.99 | 6.19 | 9.69 |

The chemical and physical data of other products having the general formula I and of their salts of addition with the acids, inclusive of the quaternary ammonium salts, prepared by the methods according to the invention, are reported in Table I. The chemical and physical data of the intermediate products having the formulae II and III, respectively, are reported in Tables II and III.

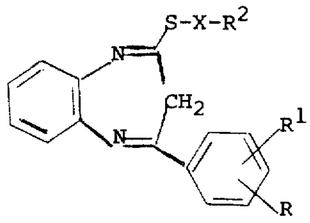

TABLE I

| Compound No. | R | $R^1$ | $R^2$ | X | Crystallization solvent | Melting point °C |
|---|---|---|---|---|---|---|
| 52 | H | H | $N(CH_3)_2$ | $CH_2CH_2$ | methyl alcohol | 182 |
| 53 | " | " | $N(C_2H_5)_2$ | " | isopropyl alcohol | 152 |
| 54 | " | " | " | " | ethyl alcohol | 180 |
| 55 | " | " | " | $CH_2CH_2CH_2$ | ethyl alcohol-ethyl ether | 85 |
| 56 | " | " | " | " | dimethyl ketone | 158 |
| 57 | " | " | 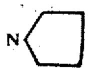 | $CH_2CH_2$ | isopropyl alcohol-ethyl ether | 192–193 |
| 58 | " | " | " | " | dimethyl ketone | 177–178 |
| 59 | " | " | 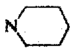 | " | isopropyl alcohol-ethyl ether | 181 |
| 60 | H | H | 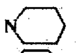 | $CH_2CH_2$ | isopropyl alcohol | 186 |
| 61 | " | " | 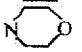 | " | isopropyl alcohol-ethyl ether | 208 |
| 62 | " | " | " | " | methyl alcohol | 177 |
| 63 | " | " | 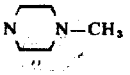 | " | " " | 172 |
| 64 | " | " | " | " | methyl alcohol-ethyl ether | 121–122 |

TABLE I-continued

| Compound No. | R | R¹ | R² | X | Crystallization solvent | Melting point °C |
|---|---|---|---|---|---|---|
| 65 | " | " | " | $CH_2CH_2$ | methyl alcohol | 170 |
| 66 | " | 4—$CH_3$ | $N(C_2H_5)_2$ | " | petroleum ether | 59-60 |
| 67 | " | " | " | " | ethyl acetate | 157 |
| 68 | " | " | " | " | ethyl alcohol | 183 |
| 69 | " | 4—$CH_3O$ | " | " | isopropyl alcohol-ethyl ether | 167 |
| 70 | " | " | " | " | ethyl alcohol | 183 |
| 71 | H | 4—Br | $N(C_2H_5)_2$ | $CH_2CH_2$ | ethyl acetate | 154 |
| 72 | " | " | " | " | ethyl alcohol | 185 |
| 73 | " | 4—$CH_3S$ | " | " | ethyl acetate | 164 |
| 74 | " | " | " | " | methyl alcohol | 195 |
| 75 | " | 4—$C_2H_5S$ | " | " | ethyl acetate | 113 |
| 76 | " | " | " | " | ethyl alcohol | 192 |
| 77 | " | 4—$nC_3H_7S$ | " | " | ethyl acetate | 136 |
| 78 | " | " | " | " | ethyl alcohol | 186 |
| 79 | " | 4—$iC_3H_7S$ | " | " | ethyl acetate | 116 |
| 80 | " | " | " | " | ethyl alcohol | 199-200 |
| 81 | " | 4—$nC_4H_9S$ | " | " | isopropyl alcohol | 42 |
| 82 | " | " | " | " | ethyl alcohol | 177 |
| 83 | " | 4—$CH_3$—$CHCH_2CH_2S$<br>\|<br>$CH_3$ | " | " | ethyl acetate | 100 |
| 84 | H | 4—$CH_3$—$CHCH_2CH_2S$<br>\|<br>$CH_3$ | $N(C_2H_5)_2$ | $CH_2CH_2$ | ethyl alcohol | 172 |
| 85 | " | 4—$nC_{12}H_{25}S$ | " | " | ethyl alcohol | 117 |
| 86 | " | " | " | " | ethyl alcohol | 142 |
| 87 | 2—$CH_3O$ | 4—$CH_3O$ | " | " | petroleum ether | 81-82 |
| 88 | " | " | " | " | ethyl alcohol | 167 |
| 89 | 2—Cl | 4— Cl | " | " | ethyl alcohol | 188 |
| 90 | " | " | " | " | ethyl alcohol | 176 |
| 91 | 3—Cl | " | " | " | ethyl acetate | 169 |
| 92 | 3—Cl | " | " | " | ethyl alcohol | 186 |
| 93 | H | 2—$C_6H_5S$ | " | " | isopropyl alcohol | 183 |
| 94 | " | " | " | " | ethyl alcohol | 197 |
| 95 | " | 4— 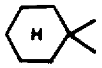 S | " | " | ethyl alcohol | 172 |
| 96 | " | " | " | " | ethyl alcohol | 188 |
| 97 | " | 4—$C_6H_5CH_2S$ | " | " | isopropyl alcohol | 141 |

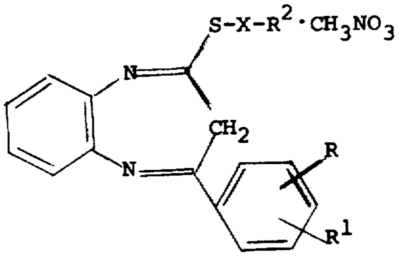

| Compound No. | X | $R_1$ | $R_1$ | $R_2$ | Crystallization solvent | M.P. |
|---|---|---|---|---|---|---|
| 98 | $CH_2CH_2$ | 4 Cl | H | $N(C_2H_5)_2$ | isopropyl alcohol | 168 |
| 99 | $CH_2CH_2CH_2$ | 4 Cl | H | $N(C_2H_5)_2$ | isopropyl alcohol | 139-140 |
| 100 | $CH_2CH_2$ | 3 Cl | H | $N(C_2H_5)_2$ | isopropyl alcohol | 142 |
| 101 | $CH_2CH_2$ | 2 Cl | H | $N(C_2H_5)_2$ | isopropyl alcohol | 170 |
| 102 | $CH_2CH_2$ | 4— 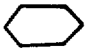 | H | $N(C_2H_5)_2$ | isopropyl alcohol | 189 |
| 103 | $CH_2CH_2$ | 4 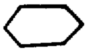 O | H | $N(C_2H_5)_2$ | isopropyl alcohol | 159 |
| 104 | $CH_2CH_2CH_2$ | 4 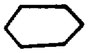 S | H | 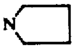 | isopropyl alcohol | 173-174 |
| 105 | $CH_2CH_2CH_2$ | 4 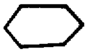 S | H | $N(C_2H_5)_2$ | isopropyl alcohol | 149-150 |
| 106 | $CH_2CH_2CH_2$ | 4 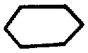 S | H | $N(CH_3)_2$ | isopropyl alcohol | 172 |
| 107 | $CH_2CH_2$ | 4 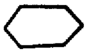 S | H | 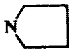 | isopropyl alcohol | 170 |
| 108 | $CH_2CH_2$ | 4 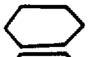 S | H | $N(CH_3)_2$ | isopropyl alcohol | 173 |
| 109 | $CH_2CH_2$ | 4 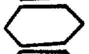 S | H | 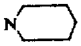 | isopropyl alcohol | 166 |
| 110 | $CH_2CH_2$ | 4 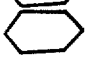 S | H | 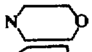 | isopropyl alcohol | 149 |
| 111 | $CH_2CH_2$ | H | H | 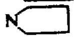 | isopropyl alcohol | 145 |
| 112 | $CH_2CH_2$ | H | H | 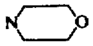 | ethyl alcohol | 172-173 |

TABLE I-continued

| Compound No. | X | $R_1$ | $R_1$ | $R_2$ | Crystallization solvent | M.P. |
|---|---|---|---|---|---|---|
| 113 | $CH_2CH_2$ | 4,methylthio | H | $N(C_2H_5)_2$ | isopropyl alcohol | 172 |
| 114 | $CH_2CH_2$ | 4,—N—butylthio | H | $N(C_2H_5)_2$ | isopropyl alcohol | 158 |
| 115 | $CH_2CH_2$ | 4,N propylthio | H | $N(C_2H_5)_2$ | isopropyl alcohol | 157 |
| 116 | $CH_2CH_2$ | 4—Br | H | $N(C_2H_5)_2$ | isopropyl alcohol | 163 |
| 117 | $CH_2CH_2$ | 4,ethylthio | H | $N(C_2H_5)_2$ | isopropyl alcohol | 157 |
| 118 | $CH_2CH_2$ | 4,isopropylthio | H | $N(C_2H_5)_2$ | isopropyl alcohol | 174 |

| Compound No. | Formula | Calculated C | Calculated H | Calculated N | Calculated S | Calculated I (+ Cl) (++$H_2O$) | Found C | Found H | Found N | Found S | Found I (+ Cl) (++$H_2O$) |
|---|---|---|---|---|---|---|---|---|---|---|---|
| 52 | $C_{19}H_{21}N_3S.CH_3$ I | 51.61 | 5.19 | 9.03 | 6.89 | 27.25 | 51.93 | 4.91 | 9.40 | 6.93 | 27.64 |
| 53 | $C_{21}H_{25}N_3S.HCl$ | HCl | | 6.75 | 10.83 | 8.24 | | | 7.01 | 10.76 | 8.42 |
| | | | 5.01 | | | | | 4.96 | | | |
| 54 | $C_{21}H_{25}N_3S.CH_3I$ | 53.54 | 5.72 | 8.39 | 6.48 | 25.72 | 53.58 | 5.68 | 8.43 | 6.52 | 25.80 |
| 55 | $C_{22}H_{27}N_3S.HCl.HCl.H_2O$ | 62.91 | 7.20 | 10.00 | 7.62 | 4.28++ | 62.48 | 6.90 | 10.30 | 7.70 | 4.30++ |
| 56 | 54.43 | 5.95 | 8.28 | 6.30 | 25.01 | 54.22 | 6.02 | 8.19 | 6.61 | 24.95 | |
| $C_{22}H_{27}N_3S.CH_3I$ | | | | | | | | | | | |
| 57 | $C_{21}H_{23}N_3S.HCl$ | 65.35 | 6.26 | 10.89 | 8.29 | | 65.15 | 6.61 | 11.09 | 8.44 | |
| 58 | $C_{21}H_{23}N_3S.CH_3I$ | 53.76 | 5.33 | 8.55 | 6.51 | 25.83 | 53.82 | 5.67 | 8.47 | 6.57 | 25.62 |
| 59 | $C_{22}H_{25}N_3S{\cdot}HCl$ | 66.08 | 6.55 | 10.51 | 8.00 | | 66.19 | 6.87 | 10.72 | 8.08 | |
| 60 | $C_{22}H_{25}N_3S{\cdot}CH_3I$ | 54.65 | 5.58 | 8.31 | 6.31 | 25.11 | 54.27 | 5.71 | 8.21 | 6.18 | 25.62 |
| 61 | $C_{21}H_{23}N_3OS.HCl$ | 62.75 | 6.01 | 10.46 | 7.96 | | 62.59 | 6.06 | 10.67 | 8.29 | |
| 62 | $C_{21}H_{32}N_3OS.CH_3I$ | 52.07 | 5.16 | 8.28 | 6.30 | 25.01 | 51.79 | 5.08 | 8.10 | 6.73 | 25.11 |
| 63 | $C_{22}H_{26}N_4S.HCl$ | 58.53 | 6.25 | 12.41 | 7.08 | | 58.18 | 6.40 | 12.37 | 7.24 | |
| 64 | $C_{22}H_{26}N_4S{\cdot}CH_3I$ | 53.07 | 5.61 | 10.77 | 6.14 | 24.39 | 52.73 | 5.58 | 10.49 | 6.29 | 23.95 |
| 65 | $C_{22}H_{26}N_4S.2CH_3I$ | 43.51 | 4.87 | 8.45 | 4.83 | 38.42 | 43.65 | 5.19 | 8.54 | 5.15 | 38.33 |
| 66 | $C_{22}H_{27}N_3S$ | 72.30 | 7.18 | | 8.76 | | 72.47 | 7.45 | | 8.86 | |
| 67 | $C_2H_{27}N_3S.HCl$ | 65.74 | 7.02 | 10.45 | 7.96 | 8.82+ | 66.19 | 7.17 | 10.58 | | 8.85+ |
| 68 | $C_{22}H_{27}N_3S.CH_3I$ | 54.43 | 6.06 | 8.28 | 6.30 | 25.01 | 54.45 | 5.74 | 8.22 | 6.41 | 25.61 |
| 69 | $C_{22}H_{27}N_3OS.HCl$ | 63.21 | 6.75 | 10.05 | 7.65 | | 62.87 | 6.81 | 9.95 | 7.64 | |
| 70 | $C_{22}H_{27}N_3OS.CH_3I$ | 52.77 | 5.77 | 8.02 | 6.11 | 24.25 | 52.58 | 5.39 | 7.97 | 6.24 | 24.36 |
| 71 | $C_{21}H_{24}BrN_3S.HCl$ | 54.03 | 5.40 | 9.00 | 6.87 | 7.59+ | 54.05 | 5.20 | 9.28 | 7.18 | 7.92+ |
| 72 | $C_{21}H_{24}BrN_3S.CH_3I$ | 46.17 | 4.75 | 7.34 | 5.60 | | 46.18 | 4.49 | 7.57 | 5.53 | |
| 73 | $C_{22}H_{27}N_3S_2.HCl$ | 60.88 | 6.50 | 9.68 | 14.77 | 8.17+ | 61.02 | 6.75 | 9.63 | 14.68 | 8.33+ |
| 74 | $C_{22}H_{27}N_2S_2.CH_3I$ | 51.20 | 5.60 | 7.79 | 11.89 | 23.52 | 51.08 | 5.33 | 8.15 | 11.93 | 23.57 |
| 75 | $C_{22}H_{29}N_3S_2.CH_6H_8O_7$ | 57.70 | 6.18 | 6.96 | 10.62 | | 57.76 | 6.40 | 6.64 | 10.72 | |
| 76 | $C_{23}H_{29}N_3S_2.CH_3I$ | 52.07 | 5.83 | 7.59 | 11.58 | 22.92 | 52.04 | 5.82 | 7.78 | 11.44 | 23.08 |
| 77 | $C_{24}H_{31}N_3S_2.HCl$ | 62.28 | 6.98 | 9.09 | 13.88 | 7.67+ | 62.50 | 6.92 | 9.32 | 13.91 | 7.99+ |
| 78 | $C_{24}H_{31}N_3S_2.CH_3I$ | 52.90 | 6.04 | 7.40 | 11.30 | 22.36 | 52.55 | 5.82 | 7.61 | 11.56 | 22.62 |
| 79 | $C_{24}H_{31}N_3S_2.C_6H_8O_7$ | 58.32 | 6.36 | 6.80 | 10.38 | | 58.08 | 6.46 | 6.51 | 10.06 | |
| 80 | $C_{24}N_{31}N_3S_2.CH_3I$ | 52.90 | 6.04 | 7.40 | 11.30 | 22.36 | 52.48 | 5.96 | 7.11 | 11.59 | 22.89 |
| 81 | $C_{25}H_{33}N_3S_2$ | 68.29 | 7.56 | 9.56 | 14.58 | | 68.47 | 7.95 | 9.38 | 14.60 | |
| 82 | $C_{25}H_{33}N_3S_2.CH_3I$ | 53.70 | 6.24 | 7.22 | 11.03 | 21.82 | 53.92 | 6.42 | 6.91 | 11.34 | 22.02 |
| 83 | $C_{26}H_{25}N_3S_2.C_6H_8O_7$ | 59.52 | 6.71 | 6.51 | 9.93 | | 59.45 | 6.26 | 6.29 | 9.88 | |
| 84 | $C_{26}H_{35}N_3S_2.CH_3I$ | 54.43 | 6.43 | 7.05 | 10.86 | 21.30 | 54.21 | 6.46 | 6.90 | 10.70 | 21.54 |
| 85 | $C_{33}H_{49}N_3S_2.C_6H_8O_7$ | 62.96 | 7.72 | 5.65 | 8.62 | | 62.56 | 8.06 | 5.67 | 8.98 | |
| 86 | $C_{33}H_{49}N_3S_2.CH_3I$ | 58.86 | 7.55 | 6.06 | 9.24 | 18.29 | 58.73 | 7.44 | 6.00 | 9.54 | 18.36 |
| 87 | $C_{23}H_{29}N_3O_2S$ | 67.12 | 7.12 | 10.21 | 7.79 | | 67.40 | 7.39 | 10.23 | 7.95 | |
| 88 | $C_{23}H_{29}N_3O_2S.CH_3I$ | 52.08 | 5.83 | 7.59 | 5.79 | 22.93 | 52.22 | 5.84 | 7.34 | 5.96 | 23.19 |
| 89 | $C_{21}H_{23}Cl_2N_3S.HCl$ | 55.21 | 5.29 | 9.20 | 7.02 | 23.28+ | 54.82 | 5.13 | 9.00 | 7.31 | 22.94+ |
| 90 | $C_{21}H_{23}Cl_2N_3S.CH_3I$ | 46.99 | 4.66 | 7.47 | 5.70 | 22.57 | 46.74 | 4.48 | 7.25 | 5.87 | 22.36 |
| 91 | $C_{21}H_{23}Cl_2N_3S.HCl$ | 55.21 | 5.29 | 9.20 | 7.02 | 23.28+ | 54.96 | 4.85 | 9.10 | 7.17 | 23.19+ |
| 92 | $C_{21}H_{23}Cl_2N_3S.CH_3I$ | 46.99 | 4.66 | 7.47 | 5.70 | 22.57 | 46.70 | 4.60 | 7.17 | 6.09 | 22.80 |
| 93 | $C_{27}H_{29}N_3S_2.HCl$ | 66.36 | 6.09 | 8.47 | 12.92 | 7.15+ | 65.16 | 5.72 | 8.30 | 13.02 | 7.39 |
| 94 | $C_{27}H_{29}N_3S_2.CH_3J$ | 55.90 | 5.34 | 6.98 | 10.66 | 21.09 | 56.00 | 5.24 | 6.82 | 10.54 | 20.90 |
| 95 | $C_{27}H_{35}N_3S_2.HCl$ | 64.58 | 7.23 | 8.37 | 12.77 | 7.06+ | 64.34 | 7.21 | 8.07 | 12.53 | 7.19+ |
| 96 | $C_{27}N_{35}N_3S_2.CH_3J$ | 55.35 | 6.30 | 6.92 | 10.55 | 20.88 | 55.40 | 6.34 | 6.76 | 10.43 | 21.25 |
| 97 | $C_{28}H_{31}N_3S_2.HCl$ | 65.92 | 6.32 | 8.24 | 12.57 | 6.95+ | 65.74 | 6.31 | 7.92 | 12.52 | 7.17+ |

| Compound No. | Formula | Calculated C | Calculated H | Calculated N | Found C | Found H | Found N |
|---|---|---|---|---|---|---|---|
| 11 98 | $C_{22}H_{27}C1n_4O_3S$ | 57.07 | 5.88 | 12.10 | 56.93 | 5.82 | 12.00 |
| 99 | $C_{23}H_{29}C1N_4O_3S$ | 57.91 | 6.13 | 11.74 | 57.84 | 6.39 | 11.56 |
| 100 | $C_{22}H_{27}C1N_4O_3S$ | 57.07 | 5.88 | 12.10 | 56.81 | 5.59 | 11.97 |
| 101 | $C_{22}H_{27}C1N_4O_3S$ | 57.07 | 5.88 | 12.10 | 56.86 | 5.91 | 11.93 |
| 102 | $C_{28}H_{32}N_4O_3S$ | 66.64 | 6.39 | 11.10 | 66.48 | 6.60 | 11.09 |
| 103 | $C_{28}H_{32}N_4O_4S$ | 64.60 | 6.19 | 10.86 | 64.32 | 6.45 | 10.65 |
| 104 | $C_{29}H_{32}N_4O_3S_2$ | 63.48 | 5.88 | 10.21 | 63.24 | 5.92 | 10.07 |
| 105 | $C_{29}H_{34}N_4O_3S_2$ | 63.25 | 6.23 | 10.17 | 63.31 | 6.23 | 9.90 |
| 106 | $C_{27}H_{30}N_4O_3S_2$ | 62.05 | 5.78 | 10.82 | 61.88 | 6.22 | 10.60 |
| 107 | $C_{28}H_{30}N_4O_3S_2$ | 62.90 | 5.65 | 10.82 | 62.70 | 5.35 | 10.72 |
| 108 | $C_{26}H_{28}N_4O_3S_2$ | 61.39 | 5.55 | 11.01 | 61.25 | 5.75 | 10.88 |
| 109 | $C_{29}H_{32}N_4O_3S_2$ | 63.48 | 5.88 | 10.21 | 63.52 | 6.02 | 10.29 |
| 110 | $C_{28}H_{30}N_4O_4S_2$ | 61.07 | 5.49 | 10.17 | 61.06 | 5.58 | 10.16 |
| 111 | $C_{22}H_{26}N_4O_3S$ | 61.96 | 6.14 | 13.14 | 61.95 | 6.40 | 12.97 |
| 112 | $C_{22}H_{26}N_4O_4S$ | 59.71 | 5.92 | 12.66 | 59.67 | 5.70 | 12.49 |
| 113 | $C_{23}H_{30}N_4O_3S_2$ | 58.20 | 6.37 | 11.80 | 58.24 | 6.77 | 11.75 |
| 114 | $C_{26}H_{36}N_4O_3S_2$ | 60.43 | 7.02 | 10.84 | 60.09 | 6.94 | 10.78 |
| 115 | $C_{25}H_{34}N_4O_3S_2$ | 59.73 | 6.81 | 11.14 | 59.53 | 6.77 | 11.37 |
| 116 | $C_{22}H_{27}BrN_4O_3S$ | 52.07 | 5.36 | 11.04 | 51.81 | 5.20 | 11.17 |
| 117 | $C_{24}H_{32}N_4O_3S_2$ | 58.99 | 6.60 | 11.46 | 58.97 | 6.46 | 11.69 |

TABLE I-continued

| Compound No. | R | R¹ | R² | | X | Crystallization solvent | | Melting point °C |
|---|---|---|---|---|---|---|---|---|
| | 118 | $C_{25}H_{34}N_4O_3S_2$ | 59.73 | 6.81 | 11.14 | 59.20 | 6.69 | 10.60 |

TABLE II

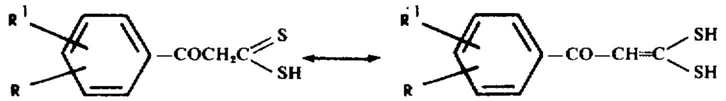

| R | R¹ | Cryst. Solvent | Melt. P. °C | Formula | Calculated C | Calculated H | Calculated N | Calculated S | Found C | Found H | Found N | Found S |
|---|---|---|---|---|---|---|---|---|---|---|---|---|
| H | 3—Cl | ethyl ether | 78-80 | $C_9H_7ClOS_2$ | 46.85 | 3.05 | | 27.74 | 46.56 | 2.81 | | 27.44 |
| H | 2—$CH_3O$ | ethyl ether | 146 | $C_{10}H_{10}O_2S_2$ | 53.10 | 4.46 | | 28.28 | 53.30 | 4.18 | | 28.47 |
| H | 3—$CH_3O$ | ethyl ether | 89-90 | $C_{10}H_{10}O_2S_2$ | 53.10 | 4.46 | | 28.28 | 52.93 | 4.11 | | 28.16 |
| H | 4—$CH_3S$ | ethyl ether | 94 | $C_{10}H_{10}OS_3$ | 49.55 | 4.16 | | 39.69 | 49.35 | 3.87 | | 39.50 |
| H | 4—$C_2H_5S$ | ethyl ether | 115 | $C_{11}H_{12}OS_3$ | 51.53 | 4.72 | | 37.52 | 51.18 | 4.37 | | 37.26 |
| H | 4—n—$C_3H_7S$ | ethyl ether | 92 | $C_{12}H_{14}OS_3$ | 53.29 | 5.22 | | 35.57 | 53.55 | 5.00 | | 35.73 |
| H | 4—i—$C_3H_7S$ | ethyl ether | 102 | $C_{12}H_{14}OS_3$ | 53.29 | 5.22 | | 35.57 | 53.50 | 5.12 | | 35.32 |
| H | 4—n—$C_4H_9S$ | ethyl ether | 96 | $C_{13}H_{16}OS_3$ | 54.89 | 5.67 | | 33.82 | 54.99 | 5.29 | | 33.74 |
| H | 4—i—$C_5H_{11}S$ | petroleum ether | 91 | $C_{14}H_{18}OS_3$ | 56.34 | 6.08 | | 32.23 | 56.73 | 6.06 | | 32.53 |
| H | 4—n—$C_{12}H_{25}S$ | ethyl ether | 59 | $C_{21}H_{32}OS_3$ | 63.57 | 8.14 | | 24.24 | 63.55 | 8.04 | | 24.20 |
| H | 4 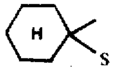 | ethyl ether | 92-93 | $C_{15}H_{18}OS_3$ | 58.06 | 5.85 | | 30.93 | 57.82 | 6.08 | | 30.48 |
| 2—Cl | 4—Cl | ethyl ether | 81-82 | $C_9H_6Cl_2OS_2$ | 40.77 | 2.28 | | 24.18 | 40.72 | 2.25 | | 24.33 |
| 3—Cl | 4—Cl | ethyl ether | 98-99 | $C_9H_6Cl_2OS_2$ | 40.77 | 2.28 | | 24.18 | 40.53 | 2.35 | | 23.88 |
| 2—$CH_3O$ | 4—$CH_3O$ | ethyl ether | 133 | $C_{11}H_{12}O_3S_2$ | 51.56 | 4.72 | | 24.98 | 51.32 | 4.56 | | 24.76 |

TABLE III

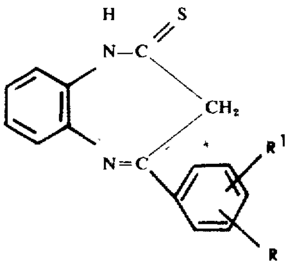

| R | R¹ | Cryst. Solvent | Melt. P. °C | Formula | Calculated C | Calculated H | Calculated N | Calculated S | $CH_3O$ |
|---|---|---|---|---|---|---|---|---|---|
| H | 2—$CH_3$ | benzene | 186 | $C_{16}H_{14}N_2S$ | 72.16 | 5.30 | 10.52 | 12.02 | |
| H | 3—$CH_3$ | ethyl acetate | 204 | $C_{16}H_{14}N_2S$ | 72.16 | 5.30 | 10.52 | 12.02 | |
| H | 4—$CH_3$ | ethyl acetate | 243-245 | $C_{16}H_{14}N_2S$ | 72.16 | 5.30 | 10.52 | 12.02 | |
| H | 2—Cl | 95% ethyl alcohol | 199 | $C_{15}H_{11}ClN_2S$ | 62.82 | 3.86 | 9.77 | 11.16 | |
| H | 3—Cl | ethyl acetate | 224-225 | $C_{15}H_{11}ClN_2S$ | 62.82 | 3.86 | 9.77 | 11.16 | |
| H | 2—$CH_3O$ | methyl alcohol | 195 | $C_{16}H_{14}N_2OS$ | 68.07 | 5.00 | 9.92 | 11.32 | 10.99 |
| H | 3—$CH_3O$ | ethyl acetate | 191 | $C_{16}H_{14}N_2$ OS | 68.07 | 5.00 | 9.92 | 11.32 | 10.99 |
| H | 4—$CH_3O$ | ethyl acetate | 233 dec | $C_{16}H_{14}N_2OS_2$ | 68.07 | 5.00 | 9.92 | 11.32 | 10.99 |
| H | 4—$CH_3S$ | ethyl acetate | 214 | $C_{16}H_{14}N_2S$ | 64.42 | 4.73 | 9.39 | 21.46 | |
| H | 4—$C_2H_5S$ | ethyl acetate | 206 | $C_{17}H_{16}N_2S_2$ | 65.37 | 5.16 | 8.97 | 20.49 | |
| H | 4—n—$C_3H_7S$ | isopropyl alcohol | 196 | $C_{18}H_{18}N_2S_2$ | 66.24 | 5.56 | 8.58 | 19.61 | |
| H | 4—i—$C_3H_7S$ | ethyl acetate | 201 | $C_{18}H_{18}N_2S_2$ | 66.24 | 5.56 | 8.58 | 19.61 | |
| H | 4—n—$C_4H_9S$ | ethyl acetate | 184 | $C_{19}H_{20}N_2S_2$ | 67.04 | 5.92 | 8.23 | 18.80 | |
| H | 4—i—$C_5H_{11}S$ | ethyl acetate | 171 | $C_{20}H_{22}N_2S_2$ | 67.78 | 6.26 | 7.91 | 18.06 | |
| H | 4—n—$C_{12}H_{25}S$ | ethyl acetate | 163 | $C_{27}H_{36}N_2S_2$ | 71.63 | 8.01 | 6.19 | 14.26 | |
| H | 4—Br | ethyl acetate | 238 | $C_{15}H_{11}BrN_2S$ | 54.40 | 3.27 | 8.46 | 9.68 | |
| 2—$CH_3$ | 4—$CH_3O$ | Benzene-petroleum ether | 179 | $C_{17}H_{16}N_2O_2S$ | 65.36 | 5.16 | 8.97 | 10.30 | |
| 2—Cl | 4—Cl | ethyl alcohol | 176 | $C_{15}H_{10}Cl_2N_2S$ | 56.09 | 3.14 | 8.72 | 9.98 | 22.07+ |
| 3—Cl | 4—Cl | ethyl acetate | 228-229 | $C_{15}H_{10}Cl_2N_2S$ | 56.09 | 3.14 | 8.72 | 9.98 | 22.07+ |
| H | 4— 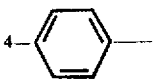 —$CH_2S$ | ethyl acetate | 197 | $C_{22}H_{18}N_2S_2$ | 70.55 | 4.84 | 7.48 | 17.12 | |
| H | 4— 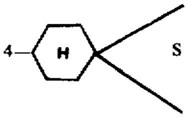 | ethyl acetate | 189-190 | $C_{21}H_{22}N_2S_2$ | 68.81 | 6.05 | 7.68 | 17.49 | |

TABLE III-continued

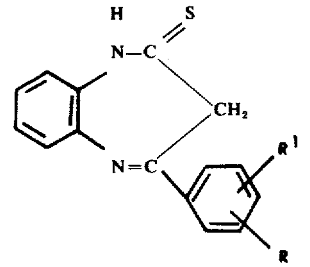

| R | $R^1$ | Cryst. Solvent | Melt. P. °C | Formula | C | H | Calculated N | S | $CH_3O$ |
|---|---|---|---|---|---|---|---|---|---|
| H | 2—$C_6H_5S$ | ethyl acetate | 214 | $C_{21}H_{16}N_2S_2$ | 69.99 | 4.48 | 7.77 | 17.76 | |
| | | | | | C | H | Found N | S | $CH_3O$ |
| H | 2—$CH_3$ | benzene | 186 | $C_{16}H_{14}N_2S$ | 72.65 | 5.42 | 10.64 | 11.68 | |
| H | 3—$CH_3$ | ethyl acetate | 204 | $C_{16}H_{14}N_2S$ | 72.08 | 5.34 | 10.28 | 12.15 | |
| H | 4—$CH_3$ | ethyl acetate | 243–245 | $C_{16}H_{14}N_2S$ | 71.56 | 5.26 | 10.38 | 12.30 | |
| H | 2—Cl | 95% ethyl alcohol | 199 | $C_{15}H_{11}ClN_2S$ | 62.78 | 3.86 | 9.73 | 11.15 | |
| H | 3—Cl | ethyl acetate | 224–225 | $C_{15}H_{11}ClN_2S$ | 63.06 | 3.83 | 9.68 | 11.16 | |
| H | 2—$CH_3O$ | methyl alcohol | 195 | $C_{16}H_{14}N_2OS$ | 67.80 | 5.02 | 9.85 | 11.67 | 11.01 |
| H | 3—$CH_3O$ | ethyl acetate | 191 | $C_{16}H_{14}N_2OS$ | 68.15 | 4.77 | 9.90 | 11.41 | 10.62 |
| H | 4—$CH_3O$ | ethyl acetate | 233 dec | $C_{16}H_{14}N_2OS_2$ | 67.97 | 4.85 | 10.13 | 11.38 | |
| H | 4—$CH_3S$ | ethyl acetate | 214 | $C_{16}H_{14}N_2S$ | 64.78 | 4.40 | 9.47 | 21.36 | |
| H | 4—$C_2H_5S$ | ethyl acetate | 206 | $C_{17}H_{16}N_2S_2$ | 65.41 | 5.15 | 8.89 | 20.35 | |
| H | 4—n—$C_3H_7S$ | isopropyl alcohol | 196 | $C_{18}H_{18}N_2S_2$ | 66.30 | 5.42 | 8.45 | 19.36 | |
| H | 4—i—$C_3H_7S$ | ethyl acetate | 201 | $C_{18}H_{18}N_2S_2$ | 65.86 | 5.24 | 8.30 | 19.70 | |
| H | 4—n—$C_4H_9S$ | ethyl acetate | 184 | $C_{19}H_{20}N_2S_2$ | 67.17 | 5.93 | 8.09 | 18.91 | |
| H | 4—i—$C_5H_{11}S$ | ethyl acetate | 171 | $C_{20}H_{22}N_2S_2$ | 67.62 | 6.18 | 7.99 | 18.03 | |
| H | 4—n—$C_{12}H_{25}S$ | ethyl acetate | 163 | $C_{27}H_{36}N_2S_2$ | 71.99 | 7.94 | 6.31 | 14.22 | |
| H | 4—Br | ethyl acetate | 238 | $C_{15}H_{11}BrN_2S$ | 54.61 | 3.08 | 8.53 | 9.98 | |
| 2—$CH_3O$ | 4—$CH_3O$ | Benzene-petroleum ether | 179 | $C_{17}H_{16}N_2O_2S$ | 65.64 | 4.86 | 9.03 | 10.42 | |
| 2—Cl | 4—Cl | ethyl alcohol | 176 | $C_{15}H_{10}Cl_2N_2S$ | 55.87 | 3.62 | 8.59 | 10.27 | 22.39 |
| 3—Cl | 4—Cl | ethyl acetate | 228–229 | $C_{15}H_{10}Cl_2N_2S$ | 55.89 | 2.91 | 8.83 | 10.00 | 21.95 |
| H | 4— 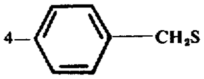 —$CH_2S$ | ethyl acetate | 197 | $C_{22}H_{18}N_2S_2$ | 70.75 | 4.82 | 7.18 | 17.36 | |
| H | 4— 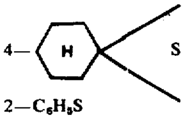 S | ethyl acetate | 189–190 | $C_{21}H_{22}N_2S_2$ | 69.11 | 6.21 | 7.68 | 17.28 | |
| H | 2—$C_6H_5S$ | ethyl acetate | 214 | $C_{21}H_{16}N_2S_2$ | 69.74 | 4.22 | 7.71 | 17.57 | |

ANTIBACTERIAL ACTIVITY

The antibacterial activity of some of the 3H-1,5-benzodiazepines having the general formula I was tested on the following microorganisms:

Escherichia coli 100, Bacillus subtilis ATCC 9466, Micrococcus pyogenes SG-511, grown in Difco nutritive gelatin; Streptococcus pyogenes A 88 grown in Difco "Brain heart infusion agar" gelatin with 5 percent difibrinated Guinea pig blood.

The results were read after 18 hours incubation at 35°-37°C.

The minimum inibitory concentrations ( μg/ml ) of the tested compounds are reported in table IV.

ANTIVIRAL ACTIVITY

Maximal tolerated dose (MTD) in the embryonated egg

The compounds were dissolved in a saline solution buffered at a pH of 7.2 containing 500 I.U. of Penicillin G and 0.5 mg of Streptomycin/ml. Descending doses of each compound dissolved in 0.1 ml were inoculated into the allantoic sac. Each dose was injected in 3 embryonated 9-day old eggs. The highest dose which did not provoke mortality within 3 days was defined as "MTD."

ANTIVIRAL METHOD

Embryonated 9-day-old leghorn hen eggs and influenza A virus (allantoic fluid containing $10^8$ – $10^9$ EID $_{50}$ (median egg-infecting dose) of egg-adapted PR8 strain) were used.

VIRUCIDAL TEST

For each dose, 0.5 MTD dissolved in 10 ml of buffered saline solution was added to $10^2$, $10^3$ or $10^4$ $EID_{95}$ and the three solutions were kept in water bath at 37°C for 1 hour. Then, the allantoic sacs of 5 eggs (for each dose) were inoculated with 0.1 ml of one of the incubated solutions.

EVALUATION OF THE ACTIVITY

The eggs were stored at 35°C for 48 hours, then at 4°C for 10 hours and finally tested for the presence of hemoagglutinin.

RESULTS TABLE IV

The numbers in the MTD column represent the maximal tolerated doses, while those in the APR8 column represent the differences between the logarithms of $EID_{95}$ (eggs infecting dose) of controls and the logarithms of $EID_{95}$ of treated eggs.

| | | Antibacterial activity | | | | Antiviral activity | |
|---|---|---|---|---|---|---|---|
| No. | Salt | B. coli | B.subtilis | M.pyogenes | S.pyogenes | MTD /coli/eggs | APR8 |
| 9 | $CH_3I$ | — | 160 | 160 | 80 | | |
| 12 | $CH_3I$ | 80 | 160 | — | 80 | | |
| 13 | HCl | 80 | 40 | 40 | 40 | | |
| 14 | $CH_3I$ | 40 | 40 | 20 | 40 | | |
| 15 | HCl | 80 | 20 | 40 | 40 | | |
| 16 | $CH_3I$ | 40 | 40 | 20 | 40 | | |
| 17 | HCl | 80x | 20 | 40 | 20x | | |
| 18 | $CH_3I$ | 20x | 20 | 40 | 10x | | |
| 19 | HCl | 80 | 40 | 40 | 40 | | |
| 20 | $CH_3I$ | 80 | 80 | 20 | 40 | | |
| 21 | HCl | 80 | 20 | 40 | 40 | | |
| 22 | $CH_3I$ | 40 | 80 | 20 | 40 | | |
| 24 | $CH_3I$ | — | — | 80 | — | | |
| 25 | HCl | — | — | 5x | 5x | | |
| 26 | $CH_3I$ | — | — | 5x | 5x | | |
| 27 | HCl | 80 | 10 | 5x | 5x | | |
| 28 | $CH_3I$ | 40x | — | 5x | 5x | 0.3 | 1 |
| 29 | HCl | 80 | — | 5x | 5x | | |
| 30 | $CH_3I$ | 2.5x | 10 | 1.25x | 1.25x | 0.3 | 1 |
| 31 | $PhCH_2Br$ | 2.5x | 10 | 0.625x | 0.625x | 0.3 | >3 |
| 34 | citrato | — | 40 | 2.5x | 2.5x | 20 | >3 |
| 35 | $CH_3I$ | — | 10 | 1.25x | 5x | 0.15 | 2 |
| 36 | $2CH_3I$ | 160 | 80 | 5x | 5x | | |
| 37 | HCl | — | 5 | 5 | 5 | | |
| 38 | $CH_3I$ | 160 | 10 | 2.5 | 10 | 2.5 | 3 |
| 39 | citrato | — | 10 | 5x | 5x | 0.3 | 3 |
| 40 | $CH_3I$ | 5x | 5 | 1.25x | 5x | 0.015 | 1 |
| 41 | HCl | — | 10 | 5x | 1.25x | 1.25 | >3 |
| 42 | $CH_3I$ | 80 | 40 | 1.25x | 1.25x | 0.15 | 3 |
| 43 | HCl | — | 1.25 | 5x | 1.25x | | |
| 44 | $CH_3I$ | 160 | 40 | 1.25x | 1.25x | 0.6 | 2 |
| 45 | citrato | — | 20 | 5x | 5x | | |
| 46 | $CH_3I$ | 160 | 20 | 5x | 1.25x | 0.3 | 2 |
| 48 | $CH_3I$ | 80 | 10 | 1.25x | 1.25x | 0.6 | >4 |
| 50 | $CH_3I$ | 160 | 10 | 5x | 1.25x | 0.15 | 2 |
| 53 | HCl | 80 | 80 | 80 | — | | |
| 57 | HCl | — | 160 | 80 | 80 | | |
| 58 | $CH_3I$ | — | — | | — | 5 | 1 |
| 59 | HCl | 160 | 80 | 80 | — | | |
| 62 | $CH_3I$ | — | — | — | — | 5 | 1 |
| 63 | 2HCl | — | — | — | — | 5 | 1 |
| 66 | HCl | — | 40 | — | 80 | 0.6 | 1 |
| 69 | HCl | — | — | — | 80 | | |
| 74 | $CH_3I$ | 40 | 10 | 20 | 10 | | |
| 82 | $CH_3I$ | 10 | 2.5 | 2.5 | 2.5 | 1 | |
| 77 | HCl | — | 5 | 10 | 5 | | |
| 78 | $CH_3I$ | 10 | 1.25 | 1.25 | 1.25 | | |
| 71 | HCl | 80 | 10 | 20 | 10 | | |
| 72 | $CH_3I$ | 20 | 20 | 10 | 20 | | |
| 76 | $CH_3I$ | 20 | 10 | 10 | 10 | | |
| 80 | $CH_3I$ | 40 | 5 | 5 | 5 | | |
| 32 | $CH_3NO_3$ | 2.5x | 10 | 1.25x | 1.25x | 0.3 | 1 |

x in a liquid medium

In the local treatment of inflammatory and infectious diseases of the oropharynx such as tonsillitis, pharyngitis, stomatitis, alveolitis, pharyngitis secondary to rhinitis, the symptomatic treatment of influenza and treatment of pre- and post-operative conditions of the oropharynx such as tonsillectomy or tooth extraction and the like, oral administration as tablets, drops, spray, lozenges, etc. of 1–2 mg. every two to three hours is generally recommended. In long-standing cases oral administration of such an amount may be every half hour.

What we claim is:

1. A compound having the following formula

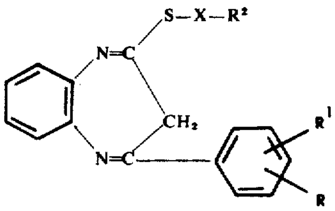

wherein

R represents hydrogen, halogen, methoxy, phenylthio or alkythio group containing 1 to 12 carbon atoms;

$R^1$ represents hydrogen, halogen, methyl, phenyl, phenoxy, alkylthio group containing 1 to 12 carbon atoms, cyclohexylthio, benzylthio or phenylthio;

$R^2$ represents a dimethylamino or diethylamino group, a morpholino, piperidino pyrrolidino or 4-methylpiperazino group; and X represents an alkylene chain containing 2 or 3 carbon atoms; a salt of addition of said compound with hydrochloric acid, citric acid or tartaric acid, and a quaternary ammonium salt of said compound formed by reaction with a methyl halide, benzyl halide or methyl nitrate.

2. Methylnitrates of 2-aminoalkylthio-3H-1,5-benzodiazepines according to claim 1 having the formula

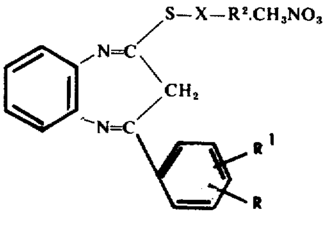

wherein R, $R^1$, $R^2$ and X have the same meanings as in claim 1.

3. 2,beta,N-diethylaminoethylthio-4,p-phenylthiophenyl-3H-1,5-benzodiazepine methyl nitrate having the formula

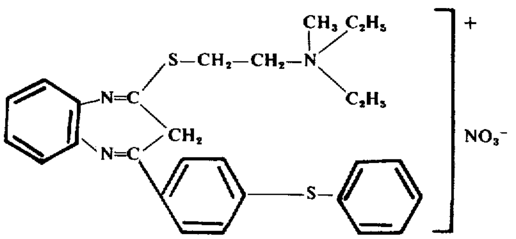

4. 2,beta,N-diethylaminoethylthio-4,p-phenylthiophenyl-3H-1,5-benzodiazepine iodomethylate having the formula

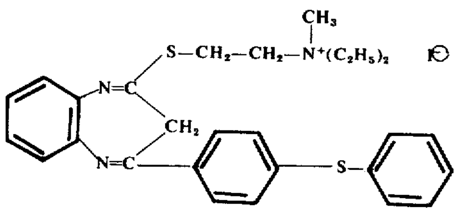

5. The method of preparing the compound of claim 1 which comprises condensing in a solvent therefor at a temperature between 40° and 130°C. for a period ranging from 5 to 20 hours an alkaline salt of a compound having the formula -continued

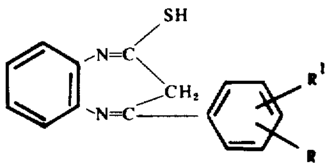

with a compound having the formula Hal-X-$R^2$, wherein Hal is a halogen atom and R, $R^1$, $R^2$ and X are as defined in claim 1.

6. The method of preparing an acid addition salt which comprises reacting the product of the method of claim 5 with hydrochloric acid, citric acid or tartaric acid.

7. The method of preparing a quaternary ammonium salt which comprises reacting the product of the method of claim 5 with an methyl halide, benzyl halide or methyl nitrate.

8. The quaternary ammonium salt of claim 1 wherein the quaterization agent is methyl iodide, methyl nitrate or benzylbromide.

9. The method of claim 5 wherein the solvent is ethyl ether, benzene or toluene.

10. A method of preparing 2-(N-substituted-)aminoalkylthio-3H-1,5-benzodiazepine methyl nitrate having the formula of claim 2 which comprises reacting in methanol at rooom temperature a 2-(N-substituted-)aminoalkylthio-3H-1,5-benzodiazepine methyl ammonium iodide with silver nitrate, and removing the resulting precipitated silver iodide while the filtered methanolic solution is evaporated to dryness, to produce methylnitrate.

11. A method of preparing 2(N-substituted)aminoalkylthio-3H-1,5-benzodiazepine methyl nitrate having the formula of claim 2, which comprises passing at room temperature for a period ranging from 1 to 4 hours a solution of 2-aminoalkylthio-3H-1,5-benzodiazepine methyl ammonium halide in 80% methanol through a column of anion exchange resin in OH form and neutralizing the resulting quaternary ammonium hydroxide methanolic solution with the theoretical quantity of nitric acid, thereafter evaporating the neutralized solution to dryness, yielding the desired methyl nitrate.

12. An acid addition salt encompassed by claim 1.

13. A quaternary ammonium salt encompassed by claim 1.

14. 2,beta,N-dialkylaminoalkylene thio-4-phenyl-3H-1,5-benzodiazepine methyl nitrate, wherein dialkyl is dimethyl or diethyl and alkylene has 2 or 3 carbon atoms.

15. 2, beta, n-dialkyl aminoalkylene thio-4-phenyl-3H-1,5-benzodiazepine iodomethylate wherein dialkyl is dimethyl or diethyl and alkylene has 2 or 3 carbon atoms.

* * * * *

UNITED STATES PATENT AND TRADEMARK OFFICE
CERTIFICATE OF CORRECTION

PATENT NO. : 3,933,793

DATED : January 20, 1976

INVENTOR(S) : DANTE NARDI et al

It is certified that error appears in the above-identified patent and that said Letters Patent are hereby corrected as shown below:

Columns 3 and 4, Formula II' should read:

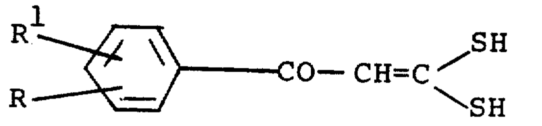

Column 16, Example 29 should read:

2,beta-N-diethylaminoethylthio-4,p-phenylthiophenyl-3H-1,5-benzodiazepine.HCl

Column 23, Example 45, line 6 should read:

(Formula I wherein R = H; $R^1$ = p-$C_6H_5S$-; $R^2$ = $N(CH_3)_2$ and X = -$CH_2CH_2$-)

Signed and Sealed this

Seventeenth Day of August 1976

[SEAL]

Attest:

RUTH C. MASON
*Attesting Officer*

C. MARSHALL DANN
*Commissioner of Patents and Trademarks*